(12) United States Patent
DiLorenzo et al.

(10) Patent No.: US 8,999,046 B2
(45) Date of Patent: *Apr. 7, 2015

(54) AIR REMOVAL CHAMBER FOR A CELL EXPANSION SYSTEM AND METHOD OF USE ASSOCIATED THEREWITH

(75) Inventors: Thomas G. DiLorenzo, Arvada, CO (US); Edward Allan Stanton, Firestone, CO (US)

(73) Assignee: Terumo BCT, Inc., Lakewood, CO (US)

( * ) Notice: Subject to any disclaimer, the term of this patent is extended or adjusted under 35 U.S.C. 154(b) by 387 days.

This patent is subject to a terminal disclaimer.

(21) Appl. No.: 13/043,933

(22) Filed: Mar. 9, 2011

(65) Prior Publication Data

US 2011/0155256 A1    Jun. 30, 2011

Related U.S. Application Data

(63) Continuation-in-part of application No. 12/606,064, filed on Oct. 26, 2009.

(60) Provisional application No. 61/322,734, filed on Apr. 9, 2010, provisional application No. 61/153,583, filed on Feb. 18, 2009, provisional application No. 61/108,773, filed on Oct. 27, 2008.

(51) Int. Cl.
*B01D 19/00* (2006.01)
*C12M 3/00* (2006.01)
(Continued)

(52) U.S. Cl.
CPC ........... *B01D 19/0063* (2013.01); *C12M 29/16* (2013.01); *C12M 25/10* (2013.01); *C12M 29/20* (2013.01); *C12M 25/12* (2013.01); *B01D 19/0042* (2013.01); *C12M 23/42* (2013.01)

(58) Field of Classification Search
CPC .......... B01D 19/0042; B01D 19/0063; C12M 23/42; C12M 29/20; C12M 25/12; C12M 29/16; C12M 25/10
USPC ............ 435/286.5, 287.3; 210/131, 188, 218; 96/155, 157, 183, 189, 204, 206
See application file for complete search history.

(56) References Cited

U.S. PATENT DOCUMENTS

| 4,231,366 A | 11/1980 | Schael |
| 4,388,944 A | 6/1983 | Honma et al. |

(Continued)

FOREIGN PATENT DOCUMENTS

| WO | 97/14962 | 4/1997 |
| WO | 99/57561 A2 | 11/1999 |

(Continued)

OTHER PUBLICATIONS

Search Report and Written Opinion issued Jul. 11, 2011, in Application No. PCT/US2011/027765.

(Continued)

*Primary Examiner* — Nathan Bowers
(74) *Attorney, Agent, or Firm* — Elizabeth J. Reagan; René A. Pereyra; John R. Merkling

(57) ABSTRACT

A cell expansion system includes an air removal chamber to provide a bubble trap so that air and/or gas bubbles do not enter the bioreactor of the cell expansion system. The air removal chamber includes a pair of ports situated at the bottom of the air removal chamber. An entrance port allows fluid to enter the air removal chamber, and an exit port allows fluid to exit the air removal chamber. In one embodiment the air removal chamber forms an element of a premounted fluid conveyance assembly for use with a cell expansion machine.

12 Claims, 15 Drawing Sheets

(51) Int. Cl.
*C12M 1/00* (2006.01)
*C12M 1/12* (2006.01)

(56) References Cited

U.S. PATENT DOCUMENTS

| | | | |
|---|---|---|---|
| 4,436,620 A | | 3/1984 | Bellotti et al. |
| 4,798,090 A | | 1/1989 | Heath et al. |
| 4,918,019 A | | 4/1990 | Guinn |
| 4,976,708 A | * | 12/1990 | Oshiyama .................... 604/408 |
| 4,997,464 A | * | 3/1991 | Kopf ................................. 96/6 |
| 5,126,238 A | | 6/1992 | Gebhard et al. |
| 5,153,133 A | | 10/1992 | Schwarz et al. |
| 5,162,225 A | | 11/1992 | Sager et al. |
| 5,178,603 A | | 1/1993 | Prince |
| 5,202,254 A | | 4/1993 | Amiot et al. |
| 5,316,905 A | | 5/1994 | Mori et al. |
| 5,424,209 A | | 6/1995 | Kearney |
| 5,958,763 A | | 9/1999 | Goffe |
| 5,985,653 A | | 11/1999 | Armstrong et al. |
| 6,001,585 A | | 12/1999 | Gramer |
| 6,048,721 A | | 4/2000 | Armstrong et al. |
| 6,096,532 A | | 8/2000 | Armstrong et al. |
| 6,228,635 B1 | | 5/2001 | Armstrong et al. |
| 6,238,908 B1 | | 5/2001 | Armstrong et al. |
| 7,270,996 B2 | | 9/2007 | Cannon et al. |
| 7,892,332 B2 | * | 2/2011 | Prisco et al. .................... 96/204 |
| 2003/0037836 A1 | | 2/2003 | Blatt et al. |
| 2004/0221719 A1 | * | 11/2004 | Wright et al. ................... 95/241 |
| 2004/0235142 A1 | * | 11/2004 | Schein et al. ............. 435/284.1 |
| 2005/0239198 A1 | | 10/2005 | Kunas et al. |
| 2006/0137663 A1 | | 6/2006 | Vaught |
| 2007/0128715 A1 | | 6/2007 | Vukasinovic et al. |
| 2008/0145925 A1 | | 6/2008 | Sakai et al. |
| 2008/0220523 A1 | | 9/2008 | Antwiler |
| 2009/0084267 A1 | | 4/2009 | Furey et al. |
| 2010/0105138 A1 | | 4/2010 | Dodd et al. |
| 2012/0088224 A1 | | 4/2012 | DiLorenzo et al. |

FOREIGN PATENT DOCUMENTS

| | | |
|---|---|---|
| WO | 2005/011569 A2 | 2/2005 |
| WO | 2007/136821 | 11/2007 |
| WO | 2007/139742 | 12/2007 |
| WO | 2007/139746 | 12/2007 |
| WO | 2007/139747 | 12/2007 |
| WO | 2007/139748 | 12/2007 |
| WO | 2008/109200 | 9/2008 |
| WO | 2008/109674 | 9/2008 |
| WO | 2008/112845 | 9/2008 |
| WO | 2008/128165 | 10/2008 |

OTHER PUBLICATIONS

PCT/US2009/062213, "International Search Report," mailed Feb. 3, 2010.
PCT/US2009/062213, "Written Opinion of the International Searching Authority," mailed Feb. 3, 2010.
PCT/US2011/055482, "International Search Report and Written Opinion," mailed Jun. 21, 2012.
Office Action, U.S. Appl. No. 12/606,064, mailed Apr. 6, 2012.
Office Action, U.S. Appl. No. 12/606,064, mailed Sep. 4, 2012.
Office Action, U.S. Appl. No. 13/269,512, Oct. 17, 2013.
Notice of Allowance and Fee(s) Due, U.S. Appl. No. 13/269,512, Sep. 15, 2014.
Office Action, U.S. Appl. No. 12/606,064, Oct. 22, 2013.
Office Action, U.S. Appl. No. 12/606,064, Apr. 1, 2014.
Requirement for Restriction/Election, U.S. Appl. No. 13/269,512, Aug. 16, 2013.
Notice of Allowance and Fee(s) Due, U.S. Appl. No. 13/269,512, May 9, 2014.
Office Action, Japanese Patent Application No. 2001-533424, Nov. 8, 2013 (English language translation included).
Office Action, U.S. Appl. No. 12/606,064, Nov. 10, 2014.

\* cited by examiner

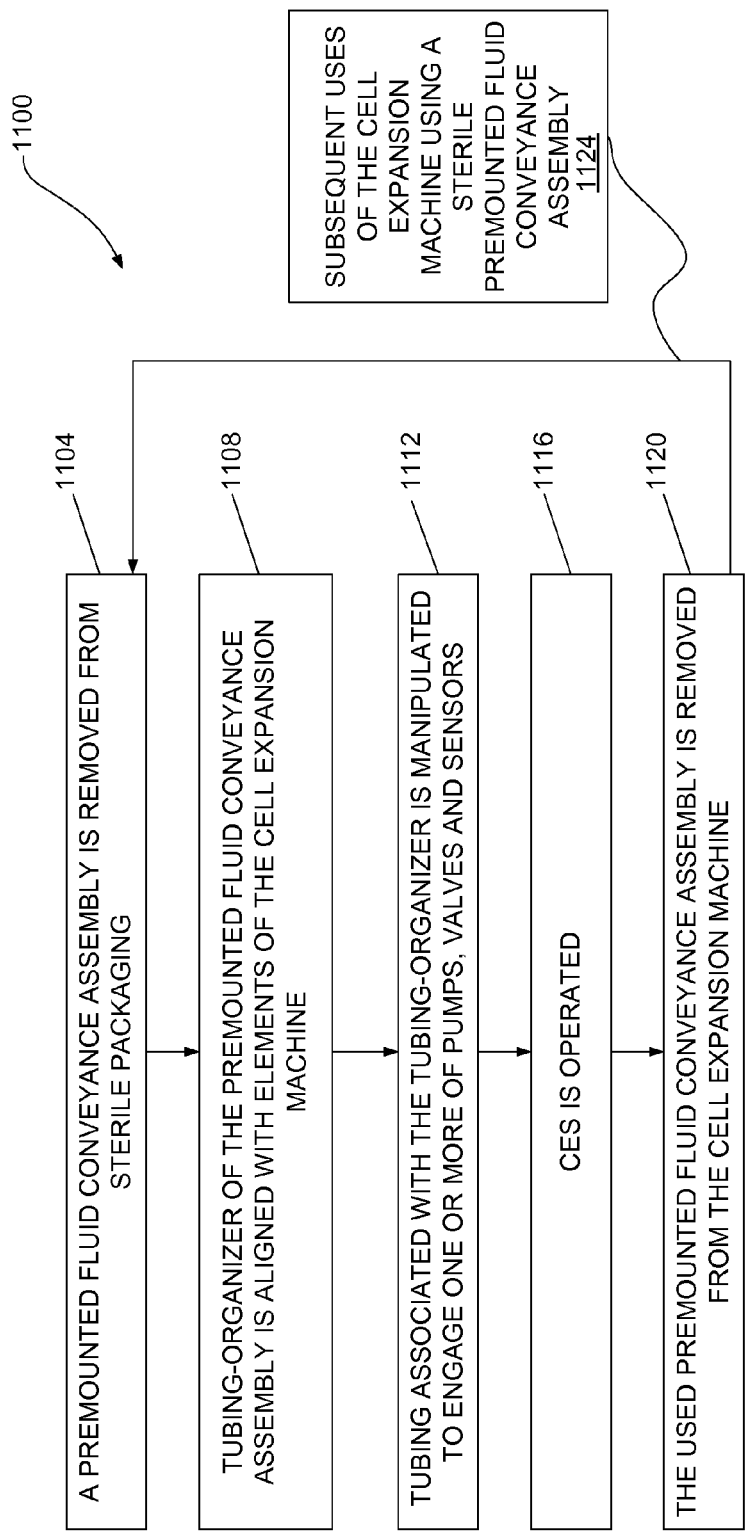

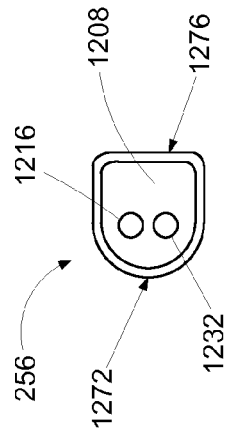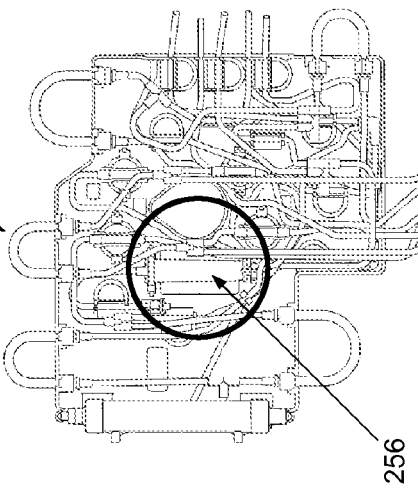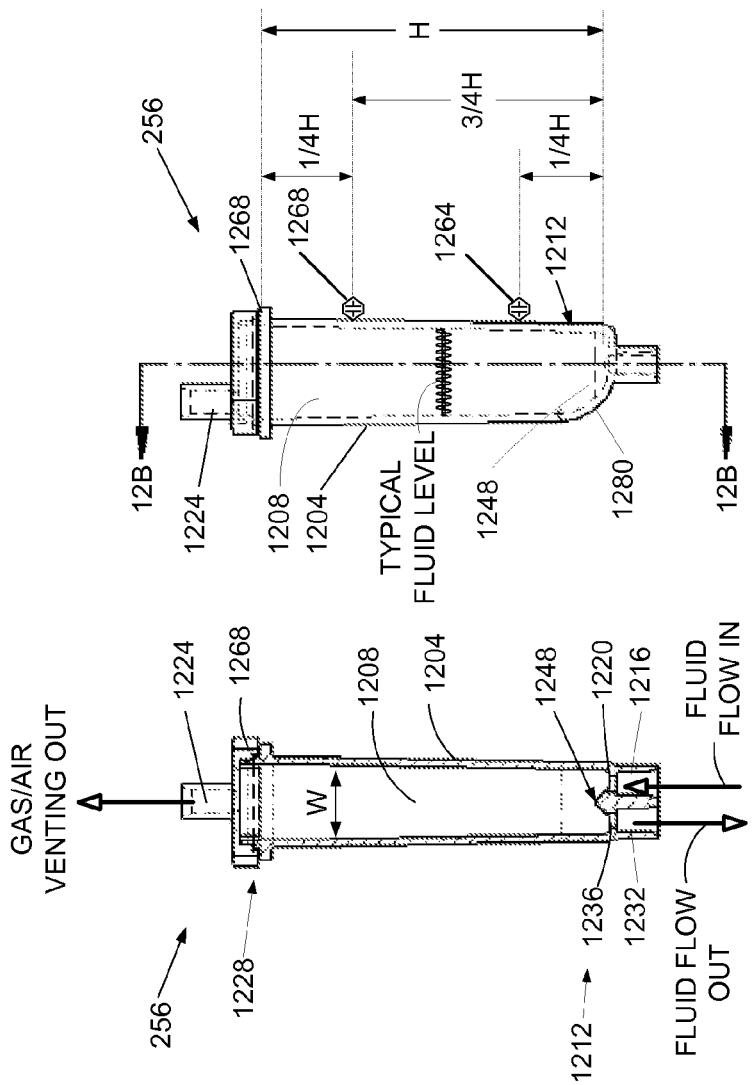

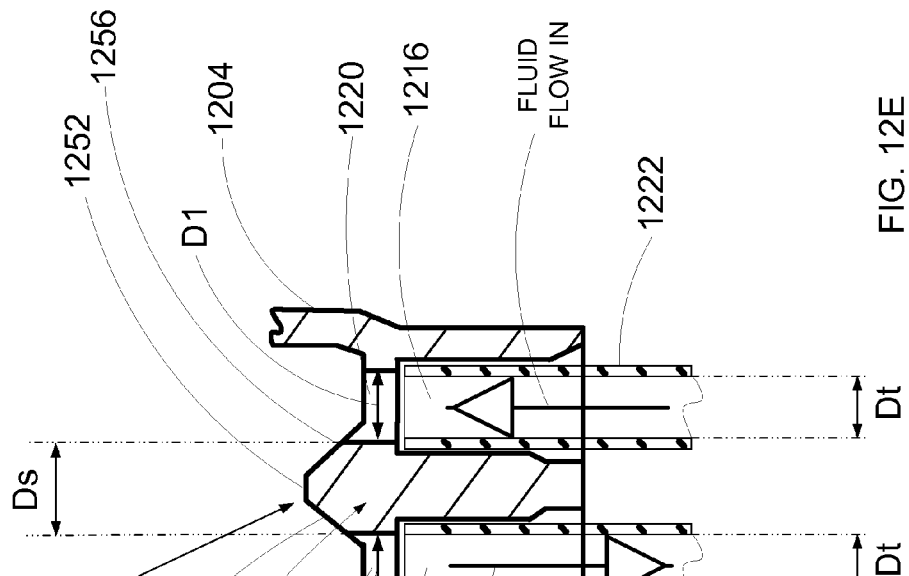
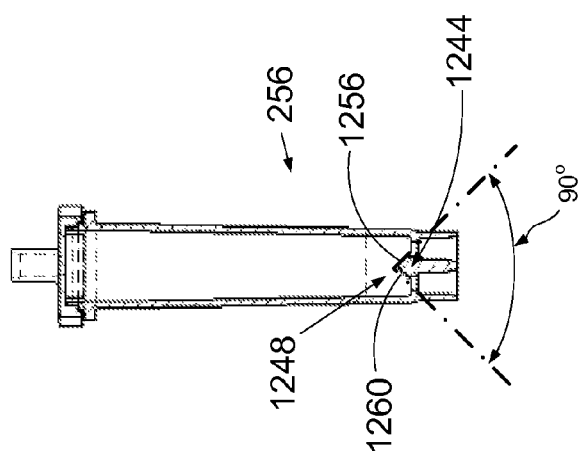
FIG. 12E
FIG. 12F

AIR REMOVAL CHAMBER FOR A CELL EXPANSION SYSTEM AND METHOD OF USE ASSOCIATED THEREWITH

RELATED APPLICATIONS

The present application is a continuation-in-part application of pending U.S. patent application Ser. No. 12/606,064 filed on Oct. 26, 2009 that claims the benefit of U.S. Provisional Patent Application Ser. No. 61/108,773 filed on Oct. 27, 2008, and U.S. Provisional Patent Application Ser. No. 61/153,583 filed on Feb. 18, 2009; the present application also claims the benefit of U.S. Provisional Patent Application No. 61/322,734 filed on Apr. 9, 2010; the contents of the foregoing applications are incorporated herein by reference in their entirety.

FIELD

The present disclosure relates to an air removal chamber for a cell expansion system (CES), including an air removal chamber that may form part of an assembly of premounted elements that can be easily attached to a cell expansion machine forming part of a cell expansion system that is used to grow cells.

BACKGROUND

CESs are used to expand and differentiate cells. Cell expansion systems are known in the art. For example, U.S. Pat. Nos. 5,162,225 and 6,001,585 generally describe cell expansion systems designed for cell expansion.

The potential use of stem cells in a variety of treatments and therapies has achieved particular attention. Cell expansion systems can be used to grow stem cells, as well as other types of cells, such as bone marrow cells. Stem cells which are expanded from donor cells can be used to repair or replace damaged or defective tissues and have broad clinical applications for a wide range of diseases. Recent advances in the regenerative medicine field demonstrate that stem cells have properties such as proliferation and self-renewal capacity, maintenance of the unspecialized state, and the ability to differentiate into specialized cells under particular conditions.

Limiting factors associated with performing cell expansion include the sterility of elements associated with the cell expansion system and the ability of lab technicians to timely disassemble equipment associated with performing a first cell expansion followed by subsequently setting up equipment associated with performing a subsequent cell expansion. Accordingly, there is a need for an assembly and methods associated with the assembly that enable a lab technician to prepare, with relatively limited downtime, equipment necessary to conduct a second cell expansion after a first cell expansion.

In addition to the forgoing, and as those skilled in the art will appreciate, the presence of air or gas bubbles in a bioreactor is detrimental to the performance of a cell expansion system. ("Air" or "gas" bubbles are used interchangeably herein.) Accordingly, it is generally considered advantageous to limit the presence of air bubbles in a bioreactor. It is also advantageous to collect data pertaining to the fluid level in the air removal chamber. Such information is beneficial to aid in operation of the cell expansion system to ensure that air bubbles are removed from the fluid flowing through the cell expansion system. More particularly, with fluid at too low a level, the air removal chamber may be substantially empty, which can result in air bubbles being pumped into the bioreactor. In contrast, if the fluid is at too high a level in the air removal chamber, such a high fluid level can result in fluid being pumped into the vent line. Both of these scenarios are undesirable. Accordingly, it is advantageous to provide an air removal chamber that sufficiently removes air bubbles from the cell expansion system while providing fluid level sensing ability that allows for the removal of air bubbles from the cell expansion system while maintaining a proper fluid level in the air chamber to avoid detrimental effects associated with too low or too high a fluid level as described above.

The present disclosure addresses these and other needs.

SUMMARY

It is to be understood that the present invention includes a variety of different versions or embodiments, and this Summary is not meant to be limiting or all-inclusive. This Summary provides some general descriptions of some of the embodiments, but may also include some more specific descriptions of other embodiments.

Interchangeability of fluid conveyance elements is achieved by providing a premounted fluid conveyance assembly for use with a cell expansion machine. Accordingly, in at least one embodiment a premounted fluid conveyance assembly for use with a cell expansion machine is provided, the cell expansion machine including a rotatable shaft, the premounted fluid conveyance assembly comprising:
  a tubing-organizer; and
  a fluid conveyance system at least partially attached to the tubing-organizer, the fluid conveyance system comprising:
    a gas transfer module;
    a length of tubing fluidly associated with the gas transfer module; and
    a bioreactor fluidly associated with the length of tubing and the gas transfer module;
  wherein the tubing-organizer and the fluid conveyance system are adapted to be detachably-attached to the cell expansion machine.

In at least one embodiment, the tubing-organizer comprises a plurality of apertures and a plurality of tubing holders spaced across a height and a width of a wall and a perimeter of the tubing-organizer. In at least one embodiment, at least one aperture of the plurality of apertures comprises an oblong-shaped shaft access aperture adapted for engaging the cell expansion machine and the rotatable shaft.

Cell expansion machines may include a number of valves for controlling fluid flow associated with a cell expansion process. Accordingly, in at least one embodiment, a premounted fluid conveyance assembly for use with a cell expansion machine is provided, the cell expansion machine including at least one valve clamp and a rotatable shaft, the premounted fluid conveyance assembly comprising:
  a fluid conveyance system comprising:
    a gas transfer module;
    a length of tubing fluidly associated with the gas transfer module; and
    a bioreactor fluidly associated with the length of tubing and the gas transfer module; and
  a support member including a plurality of holding elements, the plurality of holding elements including a gas transfer module mounting post and a plurality of tubing guides holding at least a portion of the length of tubing, wherein the support member further comprises a shaft access aperture for allowing engagement of the bioreactor with the rotatable shaft of the cell expansion machine;

wherein the support member and the fluid conveyance system are adapted to be detachably-attached to the cell expansion machine.

In at least one embodiment, the support member comprises a valve access opening adapted for allowing contact of the at least one valve clamp with a portion of the length of tubing.

In at least one embodiment, a plurality of tubing guide slots are provided for guiding tubing between a back portion and a door of the cell expansion machine. The plurality of tubing guide slots assist with limiting or preventing pinching of the tubing when the closable door is closed against the back portion of the cell expansion machine.

Embodiments of the present invention further include one or more methods associated with using a premounted fluid conveyance assembly. Accordingly, a method of expanding cells using a cell expansion machine is provided, the method comprising;

providing a first detachably-attachable premounted fluid conveyance assembly, the first detachably-attachable premounted fluid conveyance assembly including a fluid conveyance system, wherein portions of the fluid conveyance system are mounted on a support backing, wherein the fluid conveyance system includes fluid conveyance conduit, a gas transfer module, and a bioreactor; and detachably-attaching the support backing of the first detachably-attachable premounted fluid conveyance assembly to the cell expansion machine.

In at least one embodiment, the method may further comprise removing the first detachably-attachable premounted fluid conveyance assembly from a sterile package before detachably-attaching the support backing of the first detachably-attachable premounted fluid conveyance assembly to the cell expansion machine. In at least one embodiment, the method may further comprise causing a fluid flow through at least a portion of the fluid conveyance system including into a rotatable bioreactor of the fluid conveyance system. In at least one embodiment, the method may further comprise rotating the rotatable bioreactor after detachably-attaching the support backing to the cell expansion machine. In at least one embodiment, the method may further comprise detaching the support backing of the first detachably-attachable premounted fluid conveyance assembly from the cell expansion machine, and then attaching a second detachably-attachable premounted fluid conveyance assembly to the cell expansion machine. In at least one embodiment, the cell expansion machine is not sterilized in between detaching the support backing of first detachably-attachable premounted fluid conveyance assembly from the cell expansion machine and attaching a second detachably-attachable premounted fluid conveyance assembly to the cell expansion machine. In at least one embodiment, a fluid volume needed to prime the fluid conveyance system of the first detachably-attachable premounted fluid conveyance is substantially equal to a fluid volume needed to prime the second detachably-attachable premounted fluid conveyance assembly. In at least one embodiment, the method further comprises expanding and harvesting a plurality of cells from the cell expansion machine without sterilizing the cell expansion machine.

Limiting or preventing air/gas migration within a fluid conveyance system to the bioreactor in a cell expansion system can be achieved by providing an air removal chamber with certain advantageous characteristics. Accordingly, a device for use with a cell expansion machine is provided, comprising:

a fluid containment member including a containment wall defining a fluid containment chamber therein, the fluid containment member including a plurality of apertures through the containment wall including:

(a) a first aperture and a second aperture, the first aperture and the second aperture located substantially adjacent one another and situated at a bottom of the fluid containment member and separated from one another by an aperture separator wall; and (b) a venting aperture located above the first aperture and the second aperture.

In at least one embodiment the first aperture is adapted for allowing a liquid to enter the fluid containment member, and wherein the second aperture is adapted for allowing a fluid to exit the fluid containment member. In at least one embodiment the first aperture and the second aperture are separated by a separation distance $D_s$ of less than about twice the diameter $D_1$ of the first aperture. In at least one embodiment the device may further comprise a plurality of ultrasonic fluid level sensors. In at least one embodiment a first ultrasonic fluid level sensor of the plurality of ultrasonic fluid level sensors is located at a first distance of about ¼ of a chamber height H from the bottom of the fluid containment chamber. In at least one embodiment a second ultrasonic fluid level sensor of the plurality of ultrasonic fluid level sensors is located at a second distance of about ¾ of the chamber height H from the fluid containment chamber. In at least one embodiment the aperture separator wall includes a ridge portion extending into the fluid containment chamber. In at least one embodiment the ridge portion includes a first slope face and a second slope face, wherein the first slope face is oriented an angle of about 90 degrees relative to the second slope face. In at least one embodiment a top of the ridge portion is situated below a bottom-most ultrasonic sensor, and wherein the bottom-most ultrasonic fluid level sensor is located at a first distance of about ¼ of a chamber height H from the bottom of the fluid containment chamber.

In accordance with embodiments described herein, alternative structures may be provided for achieving certain functions associated with an air removal chamber. Accordingly, a gas removal chamber for a cell expansion machine is provided, comprising:

means for containing a fluid, such as a fluid containment wall, the means for containing including a top and a bottom interconnected by a perimeter wall circumscribing a hollow region;

means for allowing fluid flow into the hollow region, such a fluid entrance aperture, the means for allowing fluid flow into the hollow region located at the bottom of the means for containing;

means for allowing fluid flow out of the hollow region, such as a fluid exit aperture, the means for allowing fluid flow out of the hollow region located at the bottom of the means for containing and substantially adjacent to the means for allowing fluid flow into the hollow region; and means for venting a gas from the hollow region, such as a vent aperture, the means for venting located above the means for allowing fluid flow into the hollow region and above the means for allowing fluid flow out of the hollow region.

In at least one embodiment the gas removal chamber may further comprise a means for separating fluid flow, such as an aperture separation wall, the means for separating fluid flow located between the means for allowing fluid flow into the hollow region and the means for allowing fluid flow out of the hollow region. In at least one embodiment the means for separating fluid flow includes a ridge portion extending into the hollow region. In at least one embodiment the ridge portion includes a first slope face and a second slope face, wherein the first slope face is oriented at an angle of about 90 degrees relative to the second slope face. In at least one embodiment a top of the ridge portion is situated below a bottom-most ultrasonic fluid level sensor, and wherein the bottom-most ultrasonic fluid level sensor is located at a first distance of about ¼ of a height H of the hollow region.

Embodiments of the present invention further include one or more methods associated with removing air or gas from a cell expansion system. Accordingly, a method of removing a gas from a cell expansion system that includes a fluid conveyance conduit is provided, the method comprising:

connecting a fluid containment member to the fluid conveyance conduit, the fluid containment member including a bubble release chamber, the fluid containment member including a first aperture and a second aperture located at a bottom of the fluid containment member and fluidly associated with the bubble release chamber, the first aperture and the second aperture located substantially adjacent one another and separated from one another by an aperture separator wall having a ridge portion extending into the bubble release chamber;

pumping a fluid from the fluid conveyance conduit through the first aperture and into the bubble release chamber;

venting a gas released from the fluid within the bubble release chamber through a vent aperture located above the first and second apertures; and causing the fluid to flow out of the second aperture.

In at least one embodiment the method may further comprise measuring a height of the fluid within the bubble release chamber. In at least one embodiment the measuring is performed by operating and monitoring at least two ultrasonic sensors located adjacent the fluid containment member. In at least one embodiment the method may further comprise using data from the at least two ultrasonic sensors to adjust a pumping rate of at least one pump in order to modify a level of the fluid within the bubble release chamber. In at least one embodiment the method may further comprise connecting the fluid containment member to a tubing-organizer before pumping the fluid from the fluid conveyance conduit through the first aperture. In at least one embodiment the method may further comprise detachably-attaching the tubing organizer to a cell expansion machine of the cell expansion system before pumping the fluid from the fluid conveyance conduit through the first aperture.

Various components are referred to herein as "operably associated." As used herein, "operably associated" refers to components that are linked together in operable fashion, and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected.

Generally, any kind of fluid, including buffers, protein-containing fluid, and cell-containing fluid can flow through the various circulations paths, inlet paths, and outlet paths. As used herein, "fluid," "media," and "fluid media" are used interchangeably.

As used herein, the term "detachably-attached" means temporarily attached, and "detachably-attachable" means adapted to be temporarily attached.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

To further clarify the above and other advantages and features of the present invention, a more particular description of the invention is rendered by reference to specific embodiments thereof which are illustrated in the appended drawings. It should be appreciated that these drawings depict only typical embodiments of the invention and are therefore not to be considered limiting of its scope. The invention is described and explained with additional specificity and detail through the use of the accompanying drawings in which:

FIG. 11 is a flow chart of a method associated with use of a premounted fluid conveyance assembly;

FIG. 12A is a side elevation view of an embodiment of an air removal chamber;

FIG. 12B is a cross-sectional view of the device shown in FIG. 12A;

FIG. 12C is a front elevation view of an air removal chamber forming part of a premounted fluid conveyance assembly;

FIG. 12D is a top elevation view of the device shown in FIG. 12A with the cap removed;

FIG. 12E is an enlarged cross-sectional view of a portion of the device shown in FIG. 12B, including portions of tubing attached to the apertures;

FIG. 12F is a cross-sectional view of the device shown in FIG. 12A, with an exemplary orientation and angle of slope faces of an upper ridge portion;

The drawings are not necessarily to scale.

DETAILED DESCRIPTION

The present disclosure is generally directed to a premounted fluid conveyance assembly for use with a cell expansion machine, wherein the premounted fluid conveyance assembly and the cell expansion machine form at least a portion of a cell expansion system. As described below, a fluid conveyance system is at least partially attached to a tubing-organizer. The fluid conveyance system comprises a number of elements, including a gas transfer module, fluid conduit (e.g., tubing), and a bioreactor. The tubing-organizer and the fluid conveyance system are an integrated unit serving as a premounted fluid conveyance assembly that is adapted to be detachably-attached to the cell expansion machine.

Figure 1:
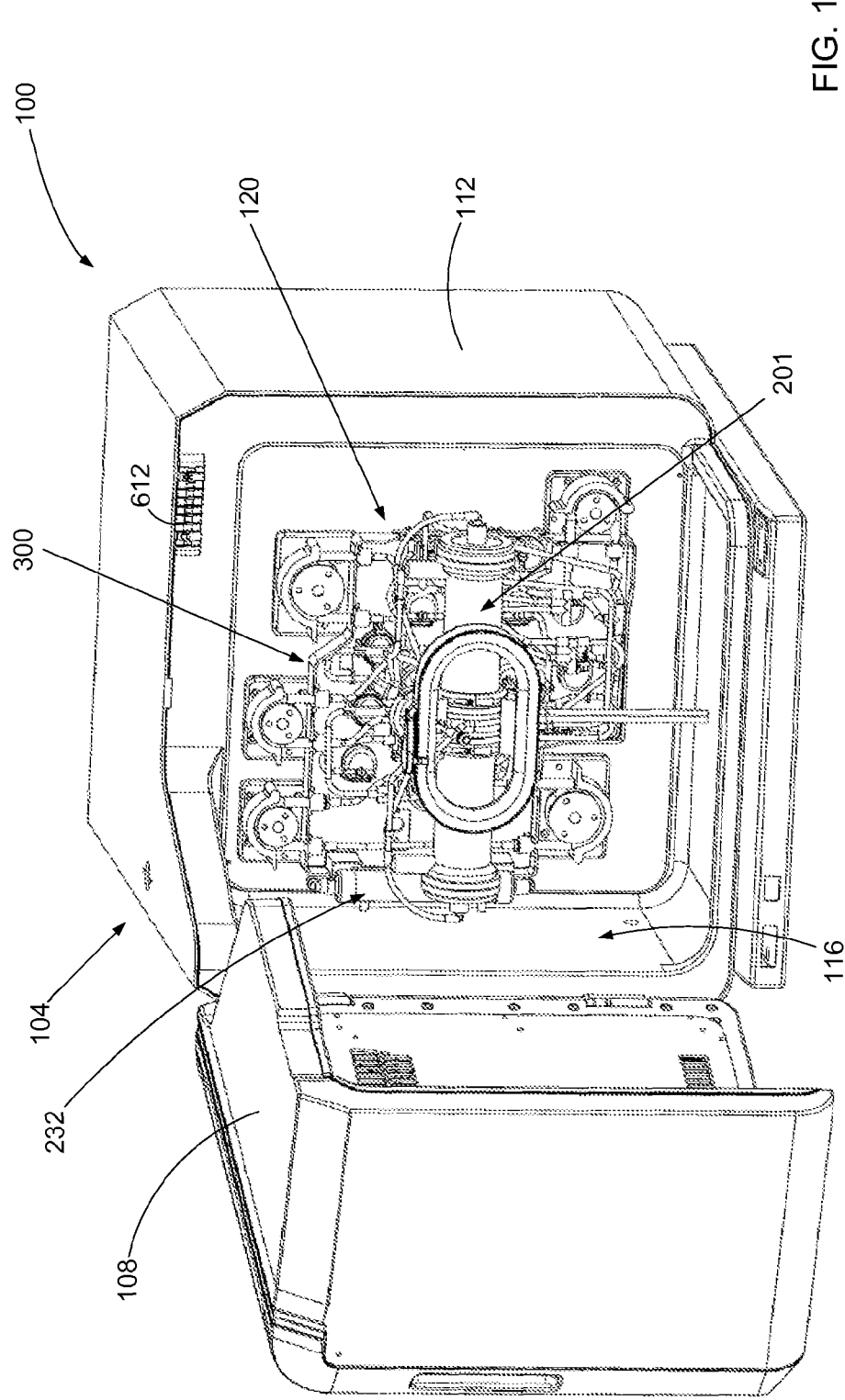
FIG. 1 is a perspective view of a cell expansion system including an embodiment of a premounted fluid conveyance assembly.

With reference now to FIG. 1, an embodiment of a CES 100 is shown. The CES 100 includes a cell expansion machine 104 that comprises a hatch or closable door 108 for engagement with a back portion 112 of the cell expansion machine 104. An interior space 116 within the cell expansion machine 104 includes features adapted for receiving and engaging a premounted fluid conveyance assembly 120. As described in detail below, the premounted fluid conveyance assembly 120 is detachably-attachable to the cell expansion machine 104 to facilitate relatively quick exchange of a new or unused premounted fluid conveyance assembly 120 at a cell expansion machine 104 for a used premounted fluid conveyance assembly 120 at the same cell expansion machine 104. Advantageously, a single cell expansion machine 104 can be operated to grow or expand a first set of cells using a first premounted fluid conveyance assembly 120, and thereafter, used to grow or expand a second set of cells using a second premounted fluid conveyance assembly 120 without needing to be sanitized between interchanging the first premounted fluid conveyance assembly 120 for the second premounted fluid conveyance assembly 120.

Figure 2:
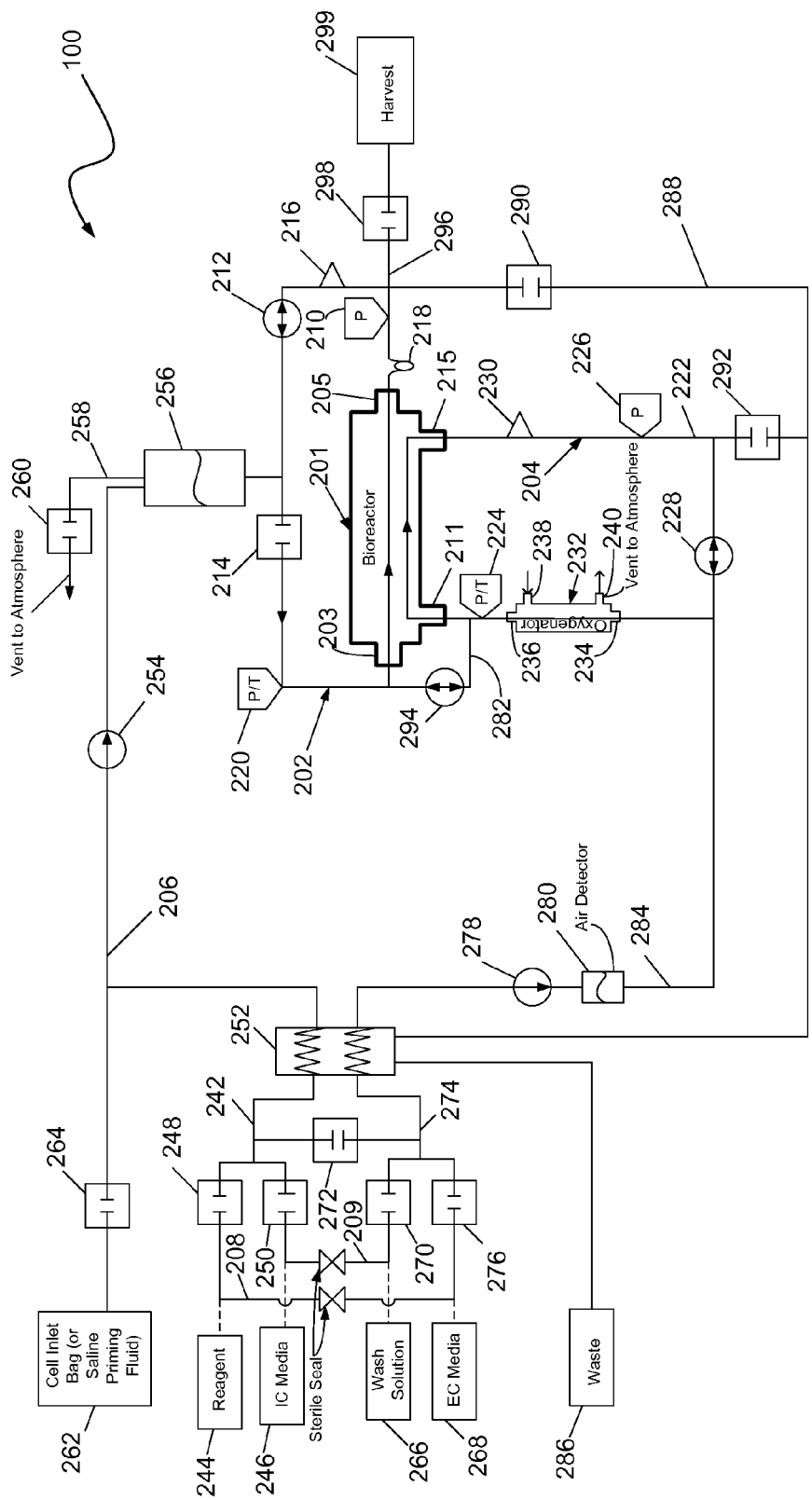
FIG. 2 is a schematic of an embodiment of a cell expansion system.

Referring now to FIG. 2, a schematic of one possible embodiment of a CES is shown. CES 100 includes first fluid circulation path 202 (also referred to as the "intracapillary loop" or "IC loop") and second fluid circulation path 204 (also referred to as the "extracapillary loop" or "EC loop"). First fluid flow path 206 is fluidly associated with bioreactor 201 to form the first fluid circulation path 202. Fluid flows into bioreactor 201 through IC inlet port 203, through hollow fibers in bioreactor 201, and exits via IC outlet port 205.

Fluid entering bioreactor via the EC inlet port 211 is in contact with the outside of the hollow fibers. Small molecules (e.g., water, oxygen, lactate, etc.) can diffuse through the hollow fibers from the interior of the hollow fiber to the EC space, or from the EC space to the IC space. Large molecular weight molecules such as growth factors are typically too large to pass through the hollow fiber membrane, and remain in the IC space of the hollow fibers. Cells can be contained within the first circulation path and/or second circulation path, and can be on either the IC side and/or EC side of the membrane.

Although bioreactor 201 is depicted as cylindrical in shape, it could have a variety of shapes, such as a rectangular cube. The bioreactor 201 can be made of any type of biocompatible polymeric material, including a substantially transparent material that permits an observer to see into the bioreactor 201. By way of example and not limitation, specifications for an exemplary bioreactor 201 for use in a CES 100 are provided in the following table.

TABLE 1

Specifications for an Exemplary Bioreactor (BioR147A Bioreactor)

| 11520 | fibers | fiber count in bioreactor |
|---|---|---|
| $215 \times 10^{-6}$ | m | fiber ID |

Referring still to FIG. 2, pressure gauge 210 measures the pressure of media leaving bioreactor 201. Media flows through IC circulation pump 212 which can be used to control the rate of media flow. Media then flows through valve 214. As those skilled in the art will appreciate, additional valves and/or other devices can be placed at various locations to isolate and/or measure characteristics of the media along portions of the fluid paths. Accordingly, it is to be understood that the schematic shown represents one possible configuration for various elements of the CES and modifications to the schematic shown are within the scope of the one or more present inventions.

With regard to the IC loop, samples of media can be obtained from sample port 216 or sample coil 218 during operation. Pressure/temperature gauge 220 disposed in first fluid circulation path 202 allows detection of media pressure and temperature during operation. Media then returns to IC inlet port 203 to complete fluid circulation path 202. Cells grown/expanded in bioreactor 201 can be flushed out of bioreactor 201 or redistributed within hollow fibers for further growth.

Second fluid circulation path 204 includes second fluid flow path 222 that is fluidly associated with bioreactor 201 in a loop. Fluid in second fluid circulation path 204 enters bioreactor 201 via EC inlet port 211, and leaves bioreactor 201 via EC outlet port 215. Media is in contact with the outside of the hollow fibers in the bioreactor 201, thereby allowing diffusion of small molecules into and out of the hollow fibers.

Pressure/temperature gauge 224 disposed in the second fluid circulation path 204 allows the pressure and temperature of media to be measured before the media enters the EC space of the bioreactor 201. Pressure gauge 226 allows the pressure of media in the second fluid circulation path 204 to be measured after it leaves the bioreactor 201. With regard to the EC loop, samples of media can be obtained from sample port 230 during operation.

After leaving EC outlet port 215 of bioreactor 201, fluid in second fluid circulation path 204 passes through EC circulation pump 228 to gas transfer module or oxygenator 232. Second fluid flow path 222 is fluidly associated with oxygenator 232 via oxygenator inlet port 234 and oxygenator outlet port 236. In operation, fluid media flows into oxygenator 232 via oxygenator inlet port 234, and exits oxygenator 232 via oxygenator outlet port 236.

The gas transfer module or oxygenator 232 adds oxygen to and removes bubbles from media in the CES. In various embodiments, media in second fluid circulation path 204 is in equilibrium with gas entering oxygenator 232. The oxygenator 232 can be any appropriately sized oxygenator known in the art. Air or gas flows into oxygenator 232 via filter 238 and out of oxygenator 232 through filter 240. Filters 238 and 240 reduce or prevent contamination of oxygenator 232 and associated media. Air or gas vented from the CES 100 can pass to the atmosphere via the oxygenator 232.

In accordance with at least one embodiment, cells and fluid media can be introduced to fluid circulation path 202 via first fluid inlet path 242. Fluid container 244 (e.g., Reagent) and fluid container 246 (e.g., IC Media) are fluidly associated with first fluid inlet path 242 via valves 248 and 250, respectively. Cells and fluid proceed through heat exchanger 252 (if used), IC inlet pump 254, and into air removal chamber 256. Air removal chamber 256 is fluidly associated with first circulation path 202. Air or gas vented from the CES 100 can pass to the atmosphere out air valve 260 via line 258 that is fluidly associated with air removal chamber 256.

Fluid container 262 (e.g., Cell Inlet Bag (or Saline Priming Fluid)) is fluidly associated with the first fluid circulation path 202 via valve 264. Additional fluid can be added to first or second fluid circulation paths 202 and 204 from fluid container 266 (e.g., Wash Solution) and fluid container 268 (e.g., EC Media). Fluid container 266 is fluidly associated with valve 270 that is fluidly associated with first fluid circulation path 202 via distribution valve 272 and first fluid inlet path 242. Alternatively, fluid container 266 can be fluidly associated with second fluid inlet path 274 by opening valve 270 and closing distribution valve 272. Likewise, fluid container 268 is fluidly associated with valve 276, that is fluidly associated with first fluid circulation path 202 via first fluid inlet path 242. Alternatively, fluid container 268 is fluidly associated with second fluid inlet path 274 by opening valve 276 and closing valve distribution 272.

In the IC loop, fluid is initially advanced by the IC inlet pump 254. In the EC loop, fluid is initially advanced by the EC inlet pump 278. An air detector 280, such as an ultrasonic sensor, may be associated with the EC inlet path 284.

In at least one embodiment, first and second fluid circulation paths 202 and 204 are connected to waste line 288. When valve 290 is opened, IC media can flow through waste line 288 that leads to the heat exchanger 252 and then to waste bag 286. Likewise, when valve 292 is opened, EC media can flow through waste line 288 that leads to the heat exchanger 252 and then to waste bag 286. The heat exchanger 252 serves to recover heat from the waste line 288 and make such heat available for heating fluids entering via the first or second fluid inlet paths 242 and 274, respectively.

Cells can be harvested via cell harvest path 296. Here, cells from bioreactor 201 can be harvested by pumping media containing the cells through cell harvest path 296 and valve 298 to cell harvest bag 299. When harvesting cells, or at other times as may be desired, distribution pump 294 can pump media through a connector path 282 located between the first and second fluid circulation paths 202 and 204.

As can be appreciated by those skilled in the art, the fluid paths discussed above and illustrated in FIG. 2 include a number of fluid conduits. To interconnect the fluid conduits and properly associate the fluid conduits to the appropriate valves, pumps, fluid bags and structures could require a lab technician to spend considerable set-up time. Moreover, the cell expansion machine remains essentially idle while the lab technician expends time and effort to disconnect the used fluid conduits, sanitize the cell expansion machine, and then reconnect new or sanitized fluid conduit to the cell expansion machine for a subsequent cell expansion cycle. In accordance with at least one embodiment of the present invention, to expedite such a process, at least some elements of the fluid conveyance system are provided in the form of a sanitized premounted assembly.

Figure 3:
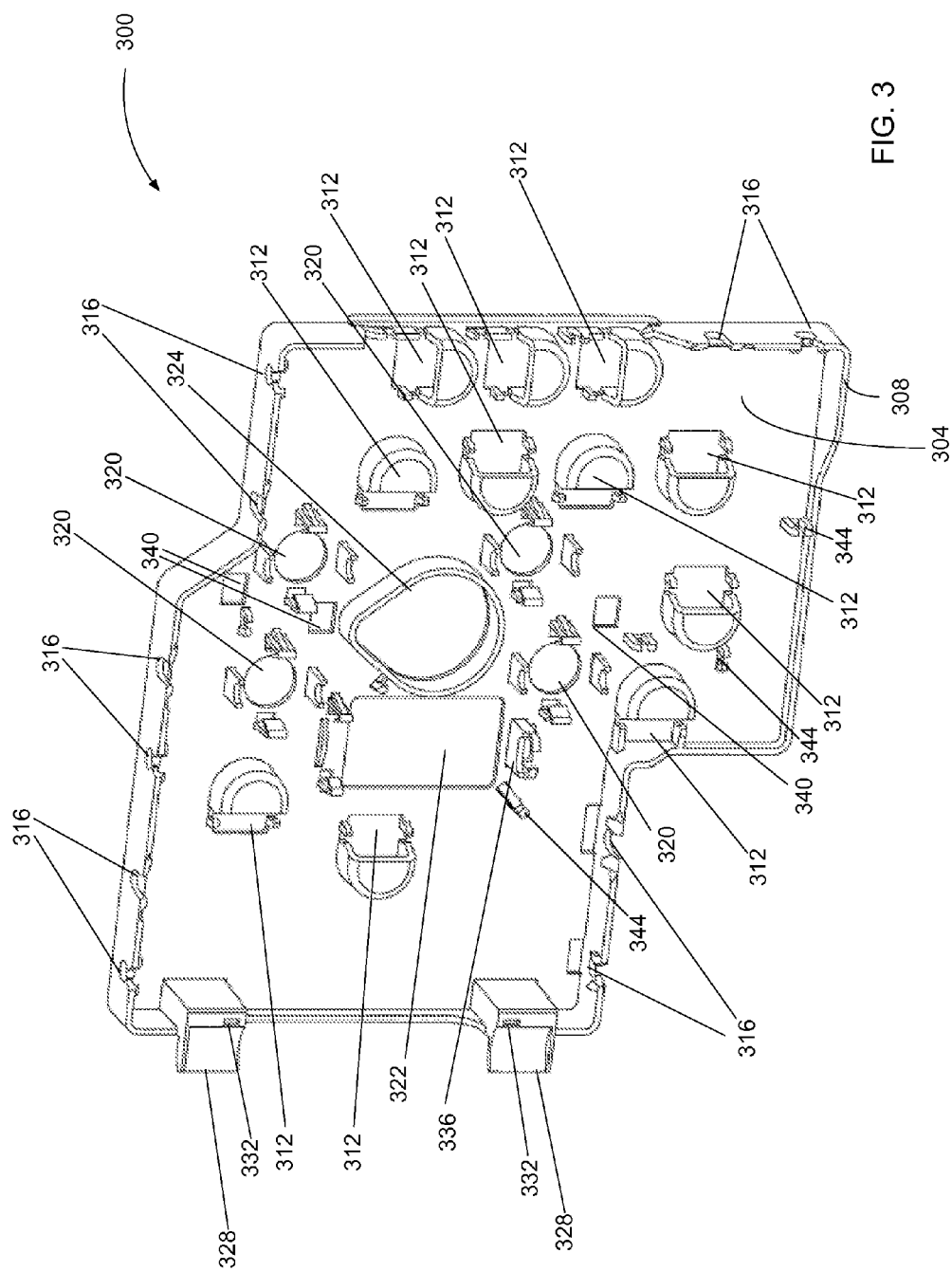
FIG. 3 is a perspective view of an embodiment of a tubing-organizer.

With reference now to FIG. 3, an embodiment of a support member or tubing-organizer 300 is shown. The tubing-organizer 300 includes a wall 304 having a perimeter 308. Residing within the wall 304 or perimeter 308 are a number of features for guiding and/or retaining elements of the fluid conveyance system. More particularly, the tubing-organizer 300 includes a plurality of valve access openings 312 for valves residing on the cell expansion machine 104. In addition, the tubing-organizer 300 also includes a plurality of pump tubing clips 316 along the perimeter 308 to hold tubing to be engaged with pumps on the cell expansion machine 104. The tubing-organizer 300 also includes a plurality of sensor ports 320. The sensor ports 320 provide access, for example, between the pressure and temperatures sensors on the cell expansion machine 104 with the sensor couplings of the fluid conveyance system. Fluid level sensor port 322 provides access through the wall 304 of the tubing-organizer 300 to allow fluid level sensors on the cell expansion machine 104 to read the level of fluid in the air removal chamber 256. The valve access openings 312, pump tubing clips 316 and sensor ports 320 are spaced apart so that the valves, pumps and sensors on the cell expansion machine 104 can engage different portions of the fluid conduit.

Still referring to FIG. 3, the tubing-organizer 300 also includes a shaft access aperture 324 for a shaft (shown in FIG. 6 and discussed below) of the cell expansion machine 104 to detachably engage the bioreactor 201. In addition, the tubing-organizer 300 further includes one or more oxygenator mounting posts 328 for receiving an oxygenator 232. The one or more oxygenator mounting posts 328 may include a fastener port 332 for receiving, by way of example, a zip tie to secure the oxygenator 232 to the oxygenator mounting post 328. The tubing-organizer 300 may further include chamber mounting post 336 for securing the air removal chamber 256. In addition, the tubing-organizer 300 may further include one or more apertures or fasteners 340 for detachably-attaching the tubing-organizer to the cell expansion machine 104. Whether present on the cell expansion machine 104 or the tubing organizer 300, such fasteners may encompass a variety of devices, including, but not limited to screws, bolts, spring-loaded or biased fasteners, movable clips or pins, and similar mechanisms or combinations of the above. The tubing-organizer 300 may further include a variety of other features, including one or more tubing clips 344 to direct tubing.

Figure 4:
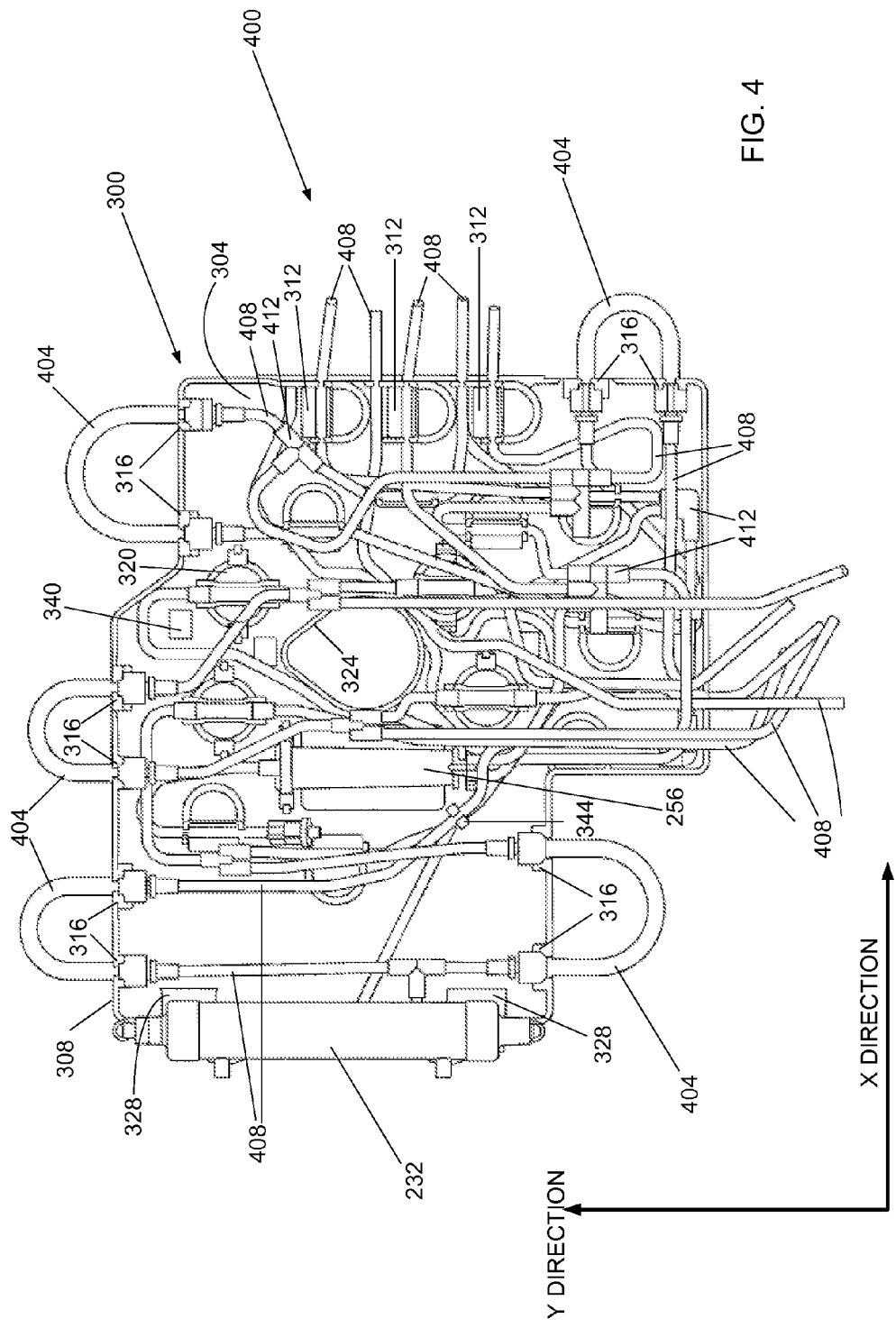
FIG. 4 is a front elevation view of the device shown in FIG. 3 with portions of a fluid conveyance system.

Referring now to FIG. 4, an embodiment of the tubing-organizer 300 is shown with a portion of the fluid conveyance system 400. For clarity, the bioreactor 201 is omitted from FIG. 4. Pump tubing conduit 404 for engaging the various pumps of the cell expansion machine 104 can be seen extending beyond and looping back to the perimeter 308 of the tubing-organizer 300. In addition, tubing 408 can be seen extending between the various valve access openings 312, pump tubing clips 316 and sensor ports 320. As needed, various tubing fittings 412 are used to interconnect sections of tubing 408.

Still referring to FIG. 4, the components of the fluid conveyance system 400 associated with the premounted fluid conveyance assembly 120 are generally distributed across the width and height of the tubing-organizer 300 in the "X" direction and "Y" direction, respectively. Such distribution of the various portions of tubing 408 and other elements of the fluid conveyance system 400 allow a lab technician to engage the premounted fluid conveyance assembly 120 to the cell expansion machine 104 in a relatively short amount of time.

Figure 5:
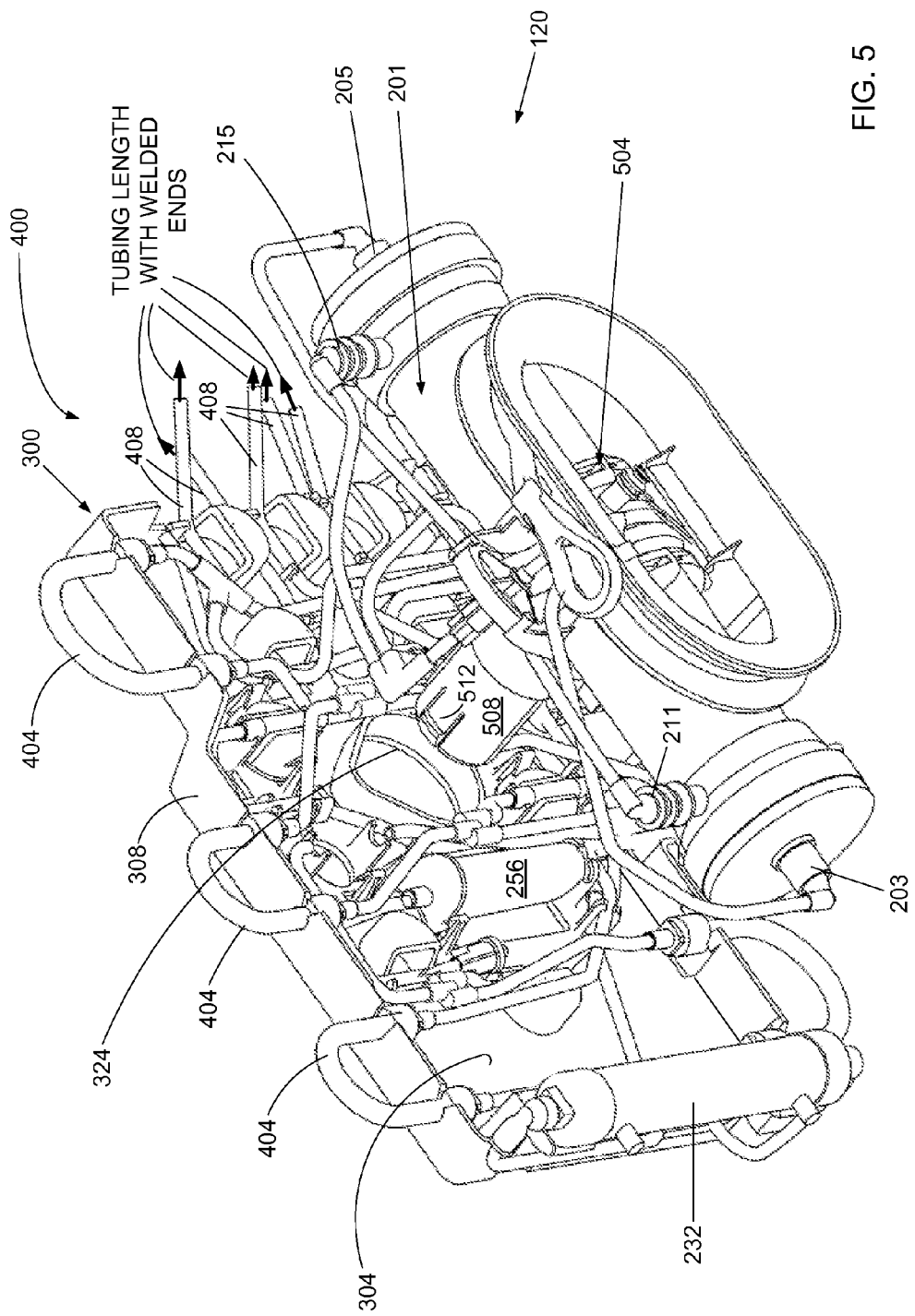
FIG. 5 is a perspective view of a premounted fluid conveyance assembly.

Referring now to FIG. 5, a perspective view of a detachably-attachable premounted fluid conveyance assembly 120 is shown. The premounted fluid conveyance assembly 120 is detachably-attachable to the cell expansion machine 104 to facilitate relatively quick exchange of a new or unused premounted fluid conveyance assembly 120 at a cell expansion machine 104 for a used premounted fluid conveyance assembly 120 at the same cell expansion machine 104. As shown in FIG. 5, the bioreactor 201 is attached to a bioreactor coupling 504 that includes a shaft fitting 508. The shaft fitting 508 includes one or more shaft fastening mechanisms, such as a biased arm or spring member 512 for engaging a shaft (shown in FIG. 6) of the cell expansion machine 104.

Referring still to FIG. 5, the premounted fluid conveyance assembly 120 typically includes tubing 408 and various tubing fittings 412 to provide the fluid paths shown in FIG. 2. Although the various media are typically provided at the site where the cell expansion machine 104 is located, the premounted fluid conveyance assembly 120 typically includes sufficient tubing length to extend to the exterior of the cell expansion machine 104 and to enable welded connections to tubing associated with the media bags.

In at least one embodiment, a plurality of premounted fluid conveyance assemblies 120 are used with a common cell expansion machine 104. Here, the plurality of premounted fluid conveyance assemblies 120 use substantially the same lengths of tubing 408 and commonly sized fluid containing structures, such as the bioreactor 201 and the oxygenator 232, so that the volume of fluid necessary to prime the fluid conveyance system 400 of the premounted fluid conveyance assemblies 120 is substantially constant.

Figure 6:
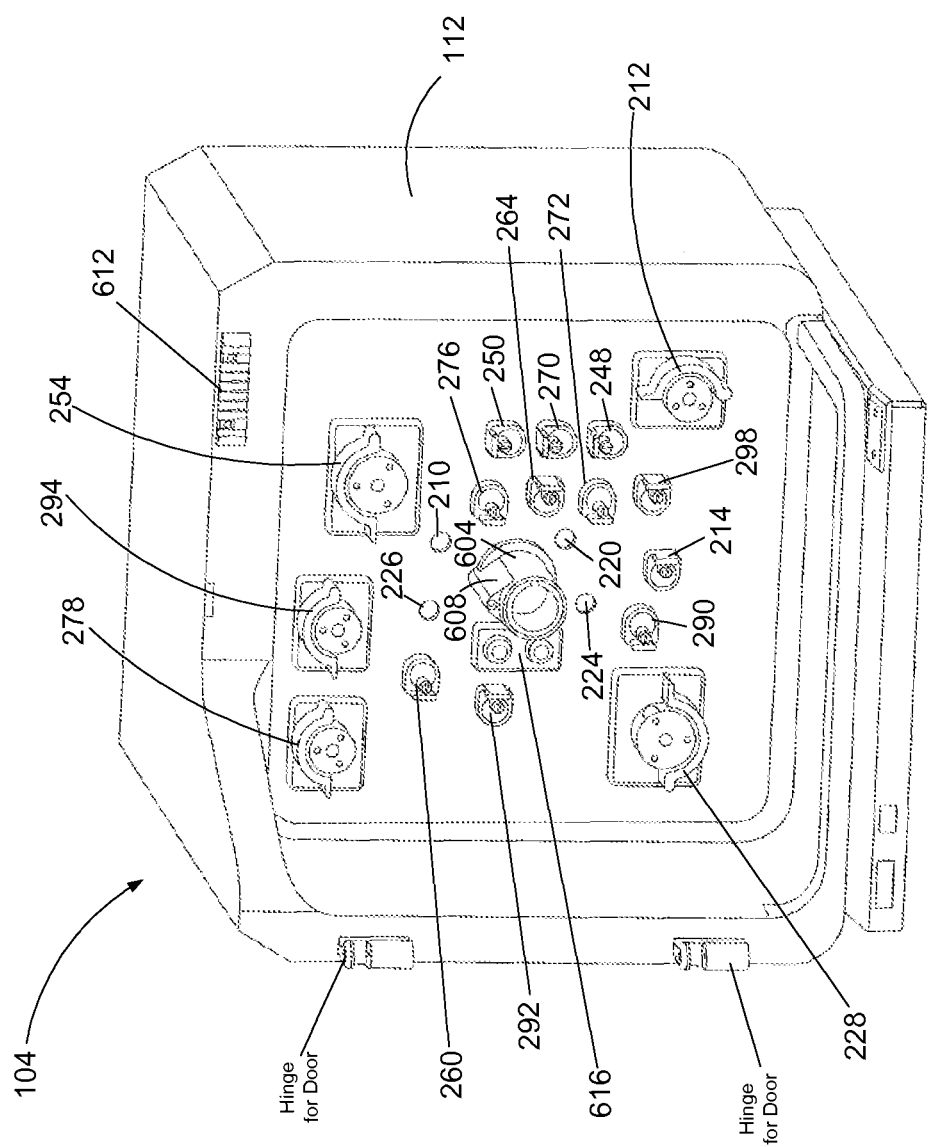
FIG. 6 is a perspective view of a back portion of a cell expansion machine.

Referring now to FIG. 6, the back portion 112 of a cell expansion machine 104 is shown prior to detachably-attaching a premounted fluid conveyance assembly 120. For clarity, the closable door 108 (shown in FIG. 1) is omitted from FIG. 6. The back portion 112 of the cell expansion machine 104 includes a number of different structures for working in combination with elements of a premounted fluid conveyance assembly 120. More particularly, the back portion 112 of the cell expansion machine 104 includes a plurality of peristaltic pumps, including the IC circulation pump 212, the EC circulation pump 228, the IC inlet pump 254, the EC inlet pump 278 and the distribution pump 294. In addition, the back portion 112 of the cell expansion machine 104 includes a plurality of valves, including the IC circulation valve 214, the reagent valve 248, the IC media valve 250, the air removal valve 260, the cell inlet valve 264, the wash valve 270, the distribution valve 272, the EC media valve 276, the IC waste valve 290, the EC waste valve 292, and the harvest valve 298. Several sensors are also associated with the back portion 112 of the cell expansion machine 104, including the IC outlet pressure sensor 210, the combination IC inlet pressure and temperature sensors 220, the combination EC inlet pressure and temperature sensors 224, and the EC outlet pressure sensor 226.

Referring still to FIG. 6, the shaft 604 for rotating the bioreactor 201 is shown. Shaped fitting 608 associated with the shaft 604 allows for proper alignment of the shaft access aperture 324 of the tubing-organizer 300 with the back portion 112 of the cell expansion machine 104. Thus, when an operator of the CES 100 attaches a new or unused premounted fluid conveyance assembly 120 to the cell expansion machine 104, the alignment is a relatively simple matter of properly orienting the shaft access aperture 324 with the shaped fitting 608 and then engaging the pump tubing conduit 404 and tubing 408 with the various corresponding features of the cell expansion machine 104.

Figure 7:
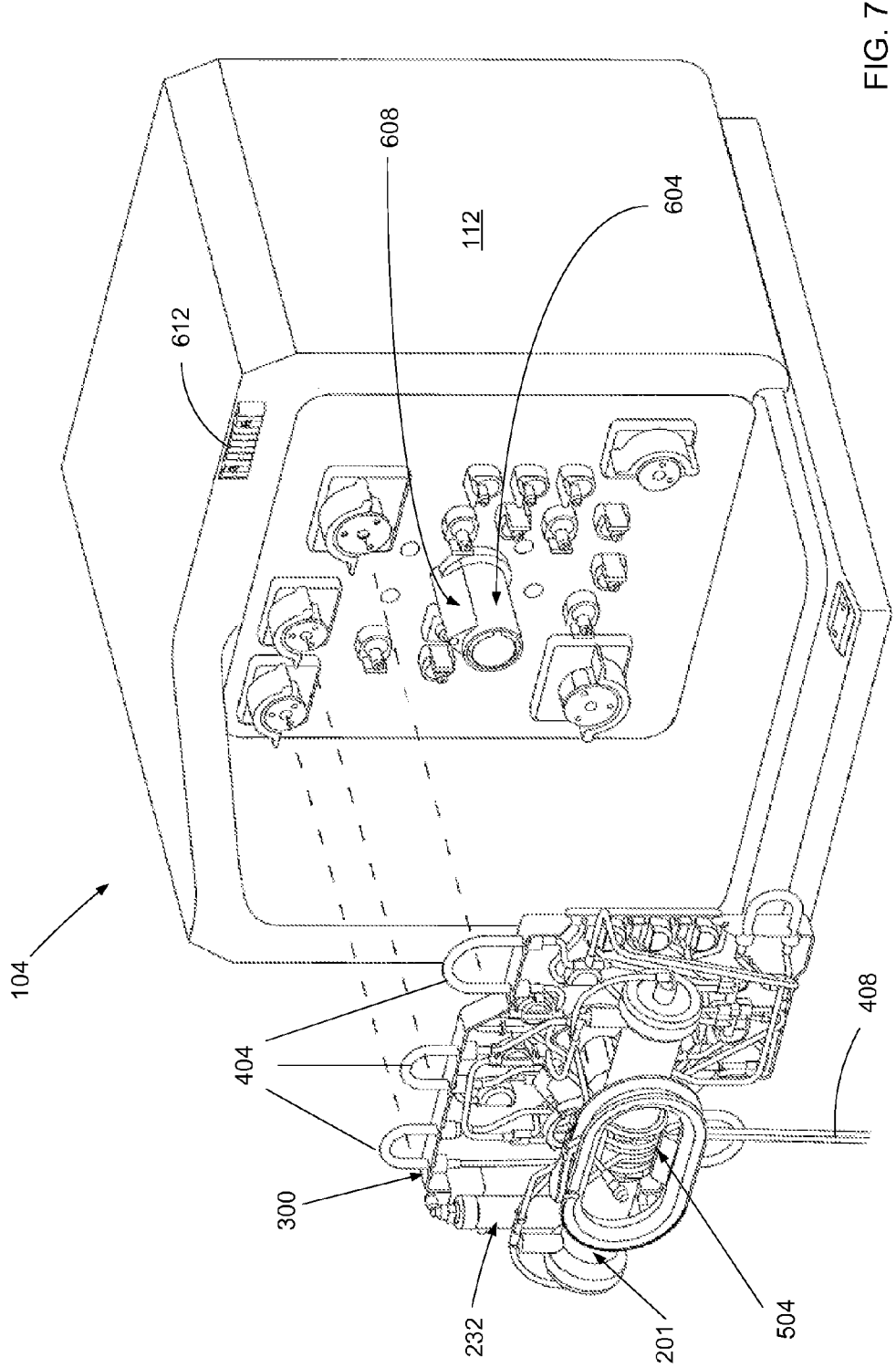
FIG. 7 is an exploded perspective view of a premounted fluid conveyance assembly aligned with the back portion of a cell expansion machine.

Referring now to FIG. 7, a premounted fluid conveyance assembly 120 is shown in spaced alignment with the back portion 112 of a cell expansion machine 104. For clarity, the closable door 108 (shown in FIG. 1) is omitted from FIG. 7. As noted above, the task associated with attaching a premounted fluid conveyance assembly 120 to the back portion 112 of the cell expansion machine 104 includes the operator aligning the shaft access aperture 324 of the tubing-organizer 300 with the shaft 604 and shaped fitting 608 of the back portion 112. The tubing 408 of the premounted fluid conveyance assembly 120 is then manipulated to engage the various valves of the cell expansion machine 104. Similarly, the pump tubing conduit 404 is manipulated to engage the various peristaltic pumps of the cell expansion machine 104. In addition, the sensors associated with the premounted fluid conveyance assembly 120 are aligned with the various sensors associated with cell expansion machine 104.

Still referring to FIG. 7, cell expansion machine 104 preferably includes a plurality of tubing guide slots 612 for exterior access of the tubing 408 to various media. The tubing guide slots 612 are located along the contact area between the closable door 108 and the back portion 112 of the cell expansion machine 104. Accordingly, the tubing guide slots 612 are substantially aligned in a planar manner with the tubing 408 residing on the premounted fluid conveyance assembly 120 when the premounted fluid conveyance assembly 120 has been detachably-attached to the back portion 112 of the cell expansion machine 104.

Figure 8:
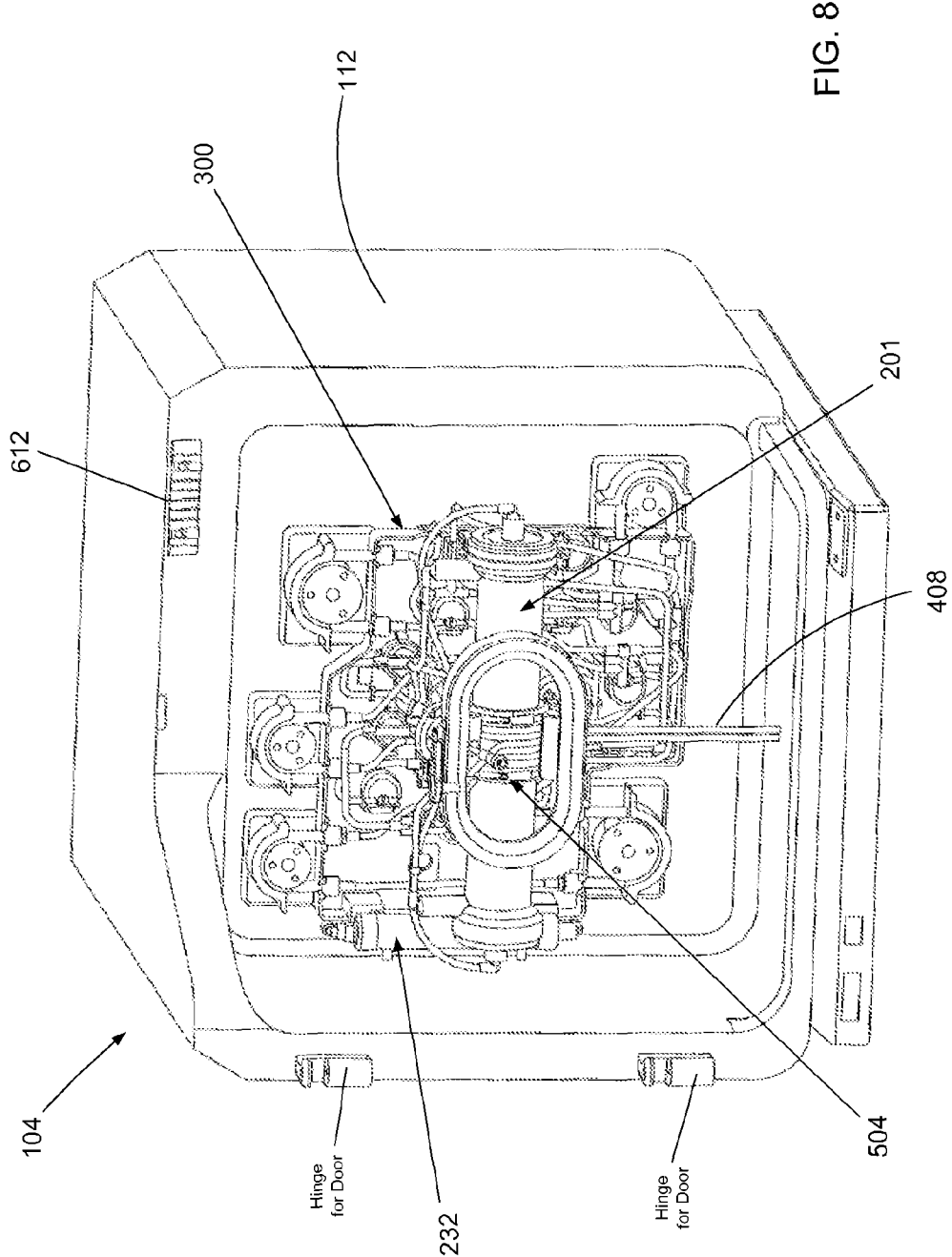
FIG. 8 is a perspective view of a premounted fluid conveyance assembly detachably-attached to the back portion of a cell expansion machine.

At FIG. 8, the premounted fluid conveyance assembly 120 has been attached to the back portion 112 of the cell expansion machine. For clarity, the closable door 108 (shown in FIG. 1) is omitted from FIG. 8. One aspect of the cell expansion machine 104 is to maintain the bioreactor, cells and media at a desirable temperature. Accordingly, the interior space 116 of the cell expansion machine 104 may be temperature controlled. Prior to closing the closable door 108 of the cell expansion machine 104, tubing 408 is passed through the tubing guide slots 612 for exterior access of the tubing 408 to various media. As will be recognized by those skilled in the art, a number of fluid containers (e.g., media bags) can be fluidly associated with the CES 100. By way of example and not limitation, fluids can be attached to the first fluid flow path 206 by welding tubing 408 fluidly associated with the fluid container 262 to the tubing 408 associated with the first fluid flow path 206. A sterile welding device such as a TERUMO® TSCD® Sterile Tubing Welder or other appropriate device may be used.

Figure 9:
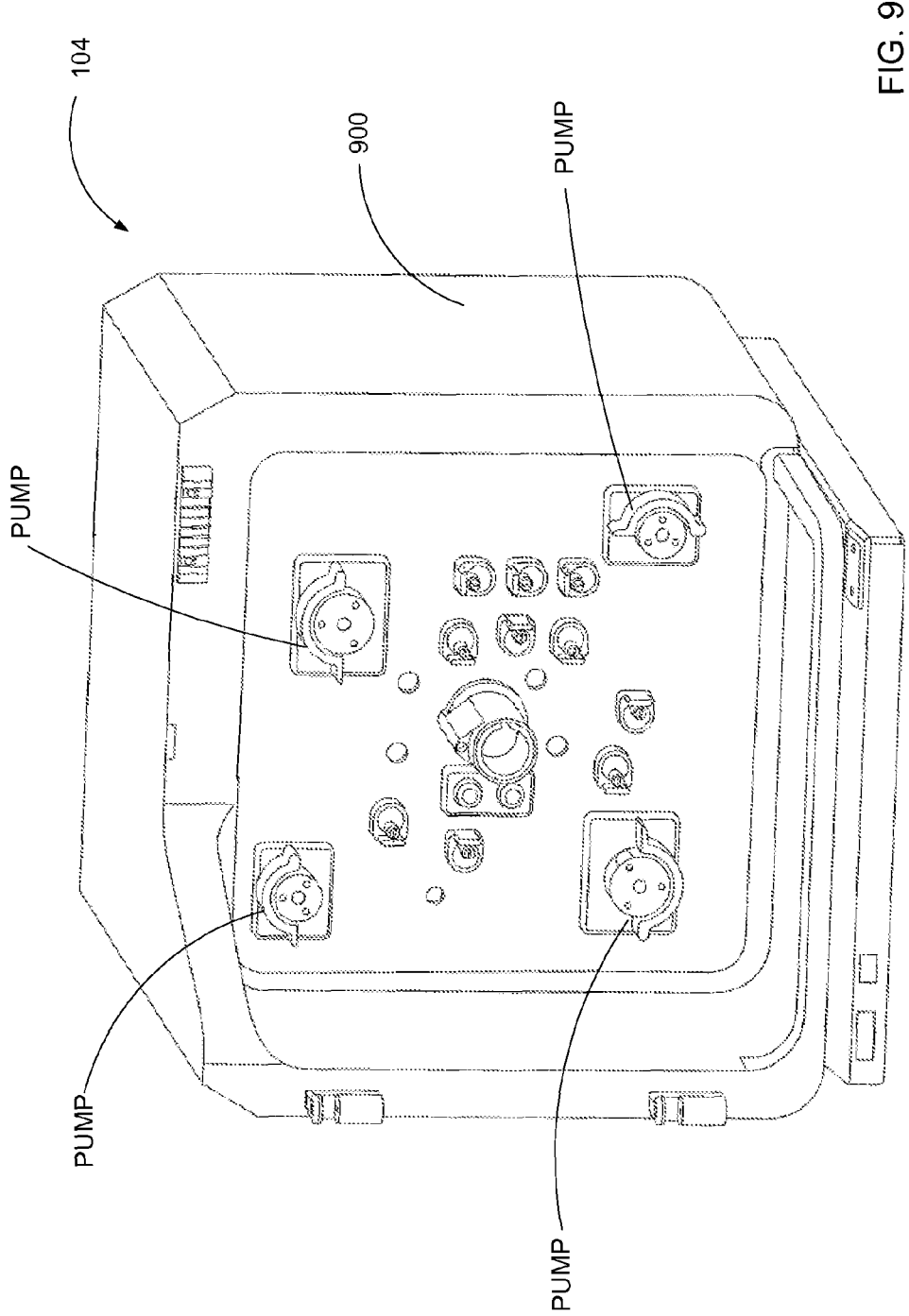
FIG. 9 is an alternative embodiment of a back portion of a cell expansion machine capable of use with an appropriately configured premounted fluid conveyance assembly.

Referring now to FIG. 9, another embodiment of a back portion 900 of a cell expansion machine 104 is shown, wherein the cell expansion machine 104 uses four peristaltic pumps rather than five pumps as described above and shown in FIGS. 1 and 6-8. Accordingly, it is to be understood that the present disclosure and the claims that follow pertain to premounted fluid conveyance assemblies 120 exhibiting tubing configurations and a tubing-organizers 300 suitable for a variety of cell expansion machines 104.

Figure 10:
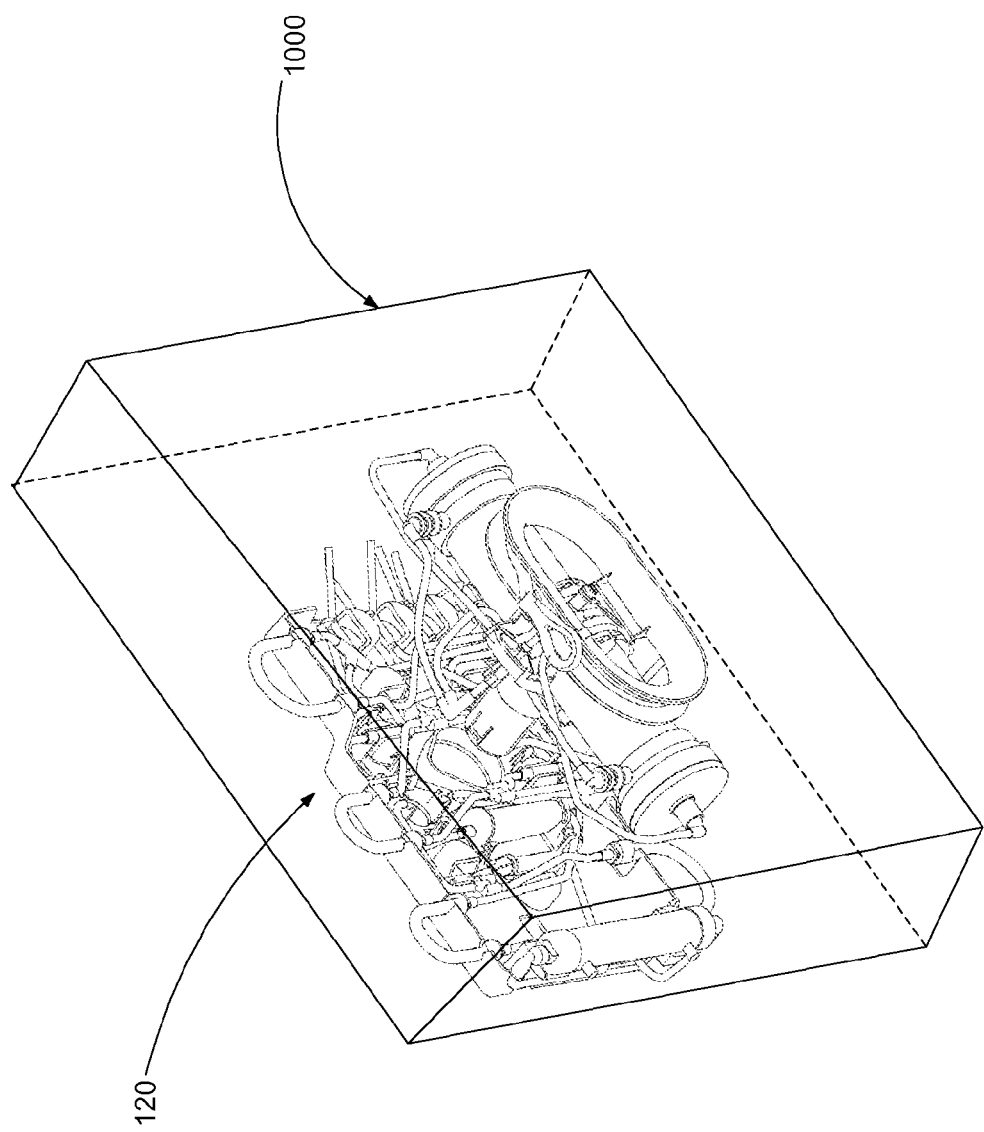
FIG. 10 is a perspective view of a premounted fluid conveyance assembly within an embodiment of sterile packaging.

With reference now to FIG. 10, after manufacturing a premounted fluid conveyance assembly 120, the completed assembly is preferably packaged in a sterile package 1000 for shipment to a facility where the premounted fluid conveyance assembly 120 will be used with a cell expansion machine 104. As those skilled in the art will appreciate, the sterile packaging 1000 may comprise a variety of different forms. As part of the manufacturing and packaging process, the premounted fluid conveyance assembly 120 is sterilized, such as by using ethylene oxide. Accordingly, the premounted fluid conveyance assembly 120 arrives prepackaged and sterile for use by a facility.

Referring now to FIG. 11, an exemplary method of use 1100 of one or more premounted fluid conveyance assemblies 120 is described. Accordingly, in at least one embodiment, at 1104 a premounted fluid conveyance assembly 120 is removed from sterile packaging 1000. At 1108, the tubing-organizer 300 is aligned with one or more elements associated with the cell expansion machine 104. By way of example, the shaft access aperture 324 of the tubing-organizer 300 is aligned with the shaped fitting 608 of the shaft 604. At 1112, pump tubing conduit 404 and tubing 408 associated with the premounted fluid conveyance assembly 120 is manipulated to engage one or more of the pumps, valves and sensors of the cell expansion machine 104. In addition, the shaft fitting 508 of the bioreactor coupling 504 is engaged with the shaft 604. At 1116, the cell expansion system 100 is operated to grow and/or expand cells in the bioreactor 201. At 1120, the used premounted fluid conveyance assembly 120 is removed from the cell expansion machine 104. As shown at 1124, subsequent uses of the cell expansion machine 104 can be performed by detachably-attaching another premounted fluid conveyance assembly 120 after a prior used premounted fluid conveyance assembly 120 is removed from the cell expansion machine 104.

In at least one embodiment, a first set of cells is grown and/or expanded in a first premounted fluid conveyance assembly 120 followed by growth and/or expansion of a second set of cells using a second premounted fluid conveyance assembly 120, wherein the cell expansion machine 104 used for growing the first set of cells and the second set of cells is not sterilized between growing the first set of cells and the second set of cells.

As those skilled in the art will appreciate, the used premounted fluid conveyance assembly 120 may be disposed of, such as by incineration, after the used premounted fluid conveyance assembly 120 is removed from the cell expansion machine 104. For the embodiments described herein, fluid circulation paths, including fluid conduit, may be constructed of any appropriate material suitable for the media, cells, and other equipment used. By way of example, one or more different types of tubing may be used in the fluid conveyance system 400. The type of tubing for engaging the peristaltic pumps of the cell expansion machine 104 may be different than the type of tubing associated with the various valves. As one example, fluid flow paths may be constructed of tubing and tubing conduits and operate in conjunction with valves, pumps and other components.

Referring now to FIGS. 12A-12F, an embodiment of an air removal chamber 256 is shown. FIG. 12C illustrates the location of the air removal chamber 256 relative to the other elements of the premounted fluid conveyance assembly 120. It is to be understood that the air removal chamber 256 may be used in a premounted fluid conveyance assembly 120 as described herein, or alternatively, the air removal chamber 256 may be used in a CES 100 that does not use a premounted fluid conveyance assembly 120.

With further reference to FIGS. 12A-12F, the air removal chamber 256 includes chamber wall 1204 defining a fluid containment chamber 1208 residing to the interior of the chamber wall 1204. In at least one embodiment, fluid enters the air removal chamber 256 at the bottom 1212 of the air removal chamber 256. More particularly, a fluid entrance port 1216 is situated at the bottom 1212 of the air removal chamber 256 such that fluid flowing into the air removal chamber 256 enters the fluid containment chamber 1208 moving upward. By way of example, and with reference here to FIG. 12E, a fluid entrance tube 1222 is connected to the air removal chamber 256 at the fluid entrance port 1216. The fluid entrance tube 1222 delivers fluid to the air removal chamber 256. In use, fluid entering the fluid containment chamber 1208 of the air removal chamber 256 passes through fluid entrance aperture 1220. Fluid moves within the fluid containment chamber 1208 releasing any air bubbles that then vent through vent aperture 1224 (and air valve 260) located at the top 1228 of the air removal chamber 256.

Referring still to FIGS. 12A-12F, fluid exits the fluid containment chamber 1208 of the air removal chamber 256 by way of fluid exit port 1232 located at the bottom 1212 of the air removal chamber 256. In use, fluid flowing out of the air removal chamber 256 exits the fluid containment chamber 1208 moving downward. In at least one embodiment, fluid is removed from the air removal chamber 256 using a peristaltic pump located downstream of the air removal chamber 256. Fluid exiting the fluid containment chamber 1208 of the air removal chamber 256 passes through fluid exit aperture 1236 and exits the air removal chamber 256 by way of fluid exit tubing 1240 connected to the air removal chamber 256 at the fluid exit port 1232.

As best seen in FIG. 12E, the fluid entrance aperture 1220 and the fluid exit aperture 1236 are separated by an aperture separator wall 1244. In accordance with at least one embodiment, the aperture separator wall 1244 extends into the fluid containment chamber 1208 and includes an upper ridge portion 1248. Accordingly, a ridge top 1252 extends above the adjacent fluid entrance aperture 1220 and the fluid exit aperture 1236. The upper ridge portion 1248 assists in limiting premature removal of fluid from the air removal chamber 256. In accordance with at least one embodiment, the upper ridge portion 1248 of the aperture separator wall 1244 includes a first slope face 1256 and a second slope face 1260. In one embodiment, and by way of example and not limitation, and as best seen in FIG. 12F, the first and second slope faces 1256 and 1260 are oriented at approximately 90 degrees to each other. The aperture separator wall 1244 and upper ridge portion 1248 may include alternate geometries from those depicted in the figures, and such variations are within the scope of the present invention.

Aspects of one or more elements described herein assist with limiting the unwanted collection of cells at various points in the fluid conveyance system 400 when the CES 100 is placed in operation. With further reference to FIG. 12E, and in accordance with at least one embodiment, an aperture diameter D1 of the fluid entrance aperture 1220 is substantially equal to the inside tube diameter Dt of the fluid entrance tube 1222. In addition, an aperture diameter D2 of the fluid exit aperture 1236 is substantially equal to the inside tube diameter Dt of the fluid exit tube 1240. To provide sufficient separation of fluid entering the air removal chamber 256 from fluid exiting the air removal chamber, the separation distance Ds between the fluid entrance aperture 1220 and the fluid exit aperture 1236 is greater than the aperture diameter D1 or the aperture diameter D2, that is, Ds>D1 and Ds>D2.

In accordance with at least one embodiment, the air removal chamber 256 is mounted in a substantially vertical orientation, such that air or gas bubbles within the fluid rise upward away from the bottom 1212 toward the vent aperture 1224 preferably located at the top 1228 of the air removal chamber 256, or at least above the fluid entrance aperture 1220 and fluid exit aperture 1236.

Referring again to FIG. 12A, in at least one embodiment a plurality of fluid level sensors are used in combination with the air removal chamber 256. In at least one embodiment, the sensors are located on the cell expansion machine 104. More particularly, while the air removal chamber 256 is connected to a premounted fluid conveyance assembly 120 that can be detachably-attached to the cell expansion machine 104, the fluid level sensors for the air removal chamber 256 form part of the cell expansion machine 104.

In accordance with at least one embodiment, at least two sensors are used with the air removal chamber 256 to provide "high" and "low" fluid level sensing capability. Accordingly, operating protocol for the CES 100 includes monitoring the fluid level within the air removal chamber 256 and adjusting the pumping rate of the peristaltic pumps as necessary to maintain an appropriate fluid level within the fluid containment chamber 1208 of the air removal chamber. This operating protocol may include increasing or decreasing the pumping rates associated with pumps on either one or both the upstream and downstream sides of the air removal chamber 256.

With reference still to FIG. 12A, the height H of the fluid containment chamber 1208 of the air removal chamber 256 is shown. In at least one embodiment, a first fluid level sensor 1264 (or low level fluid sensor) is situated to detect a fluid level in the air removal chamber 256 at a level of approximately ¼ full or ¼ H, and a second fluid level sensor 1268 (or high level fluid sensor) is situated to detect a fluid level in the air removal chamber 256 at a level of approximately ¾ full or ¾ H. The position of the fluid level sensors 1264 and 1268 allow the fluid level within the air removal chamber 256 to be adjusted to ensure that air does not pass though the fluid exit aperture 1236 and enter the fluid exit tube 1240 at the bottom 1212 of the air removal chamber 256 because of too low a fluid level, and that fluid does not exit through vent aperture 1224 located at the top 1228 of the air removal chamber 256 because of too high a fluid level.

Figure 13:
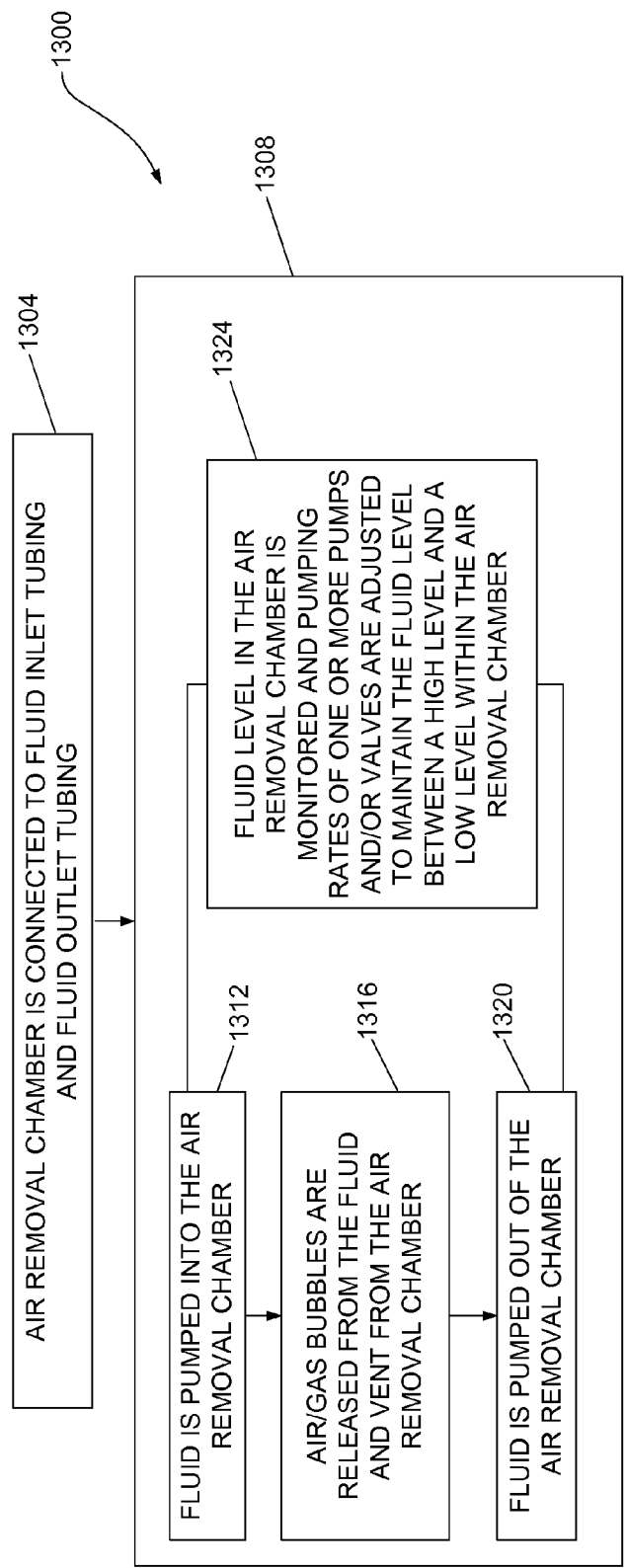
FIG. 13 is a flow chart of a portion of a method associated with an air removal chamber.

With reference now to FIG. 13, a portion of the air removal protocol 1300 associated with the air removal chamber 256 is shown. More particularly, at 1304 an air removal chamber 256 is connected to the fluid entrance tube 1222 and fluid exit tube 1240. Here, if a premounted fluid conveyance assembly 120 is used, then one or both of the tubes 1222 and 1240 may be connected to the air removal chamber 256 at an equipment assembly location that is spatially separated from the location where the air removal chamber 256 is actually put to use as part of a CES 100. At 1308, the air removal chamber 256 is used. More particularly, at 1312 fluid is pumped into the air removal chamber 256, such as via fluid entrance tube 1222. At 1316 air/gas bubbles are then released from the fluid while the fluid resides within the fluid containment chamber 1208 of the air removal chamber 256. At 1320 fluid is then pumped out of the air removal chamber, such as via fluid exit tube 1240. During the periods when fluid is being circulated through the air removal chamber 256, fluid levels are being monitored at 1324 within the air removal chamber 256. To maintain the fluid level within the air removal chamber 256 between a high level and a low level, such as at sensor locations 1264 and 1268, the fluid pumping rates both upstream and downstream of the air removal chamber 256 may be adjusted. In addition, valve positioning may also be adjusted to maintain a proper operating fluid level within the air removal chamber 256. Accordingly, data from fluid level sensors 1264 and 1268 is checked and pumping rates are adjusted. For example, if the low level fluid sensor 1264 detects "no fluid," this information is used to adjust one or more pumping rates both upstream and downstream of the air removal chamber 256 to increase the fluid level within the fluid containment chamber 1208 of the air removal chamber 256. Similarly, if the high level fluid sensor 1268 detects "fluid," this information is also used to adjust one or more pumping rates both upstream and downstream of the air removal chamber 256 to decrease the fluid level within the fluid containment chamber 1208 of the air removal chamber 256.

In at least one embodiment, fluid level detection is achieved using ultrasonic sensors. More particularly, the fluid level sensors 1264 and 1268 are discrete level sensing ultrasonic sensors. The ultrasonic sensors work on the principle that the travel time of sound between the emitter and detector drops sharply as fluid (that is mostly water) comes between the emitter and detector. Ultrasonic sensors have been found to be reliable and capable of providing data associated with discrete levels within the air removal chamber, including at the levels noted above.

With continued reference to FIGS. 12A and 12B, in at least one embodiment the fluid level sensors 1264 and 1268 are connected to the cell expansion machine 104, and remain with the cell expansion machine 104 when the premounted fluid conveyance assembly 120 is detachably-attached from the cell expansion machine 104.

The shape and relative dimensions of the air removal chamber 256 generally assist with allowing air or gas bubbles within the fluid that enters the air removal chamber 256 to rise and vent through the vent aperture 1224 before the fluid exits the fluid containment chamber 1208 through the fluid exit port 1232. In addition, the width W of the fluid containment chamber 1208 generally increases from the bottom 1212 toward the top 1228 of the air removal chamber 256. The height H of the fluid containment chamber 1208 generally is greater than a width W of the fluid containment chamber 1208. More preferably, the height H of the fluid containment chamber 1208 is preferably greater than about five times an average width of the fluid containment chamber 1208, that is, $H > 5 \times W$.

The air removal chamber includes a front 1272 and a back 1276. As depicted in FIG. 12A, the back 1276 is configured for locating in operative association with the fluid level sensors 1264 and 1268. At least a portion of the back 1276 may contain a substantially planar surface for positioning adjacent the fluid level sensors 1264 and 1268. In at least one embodiment the front 1272 includes a sloping bottom portion 1280. In at least one embodiment the vent aperture 1224 resides within a cap 1268 that is connected to the top 1228 of the air removal chamber 256.

Figure 14:
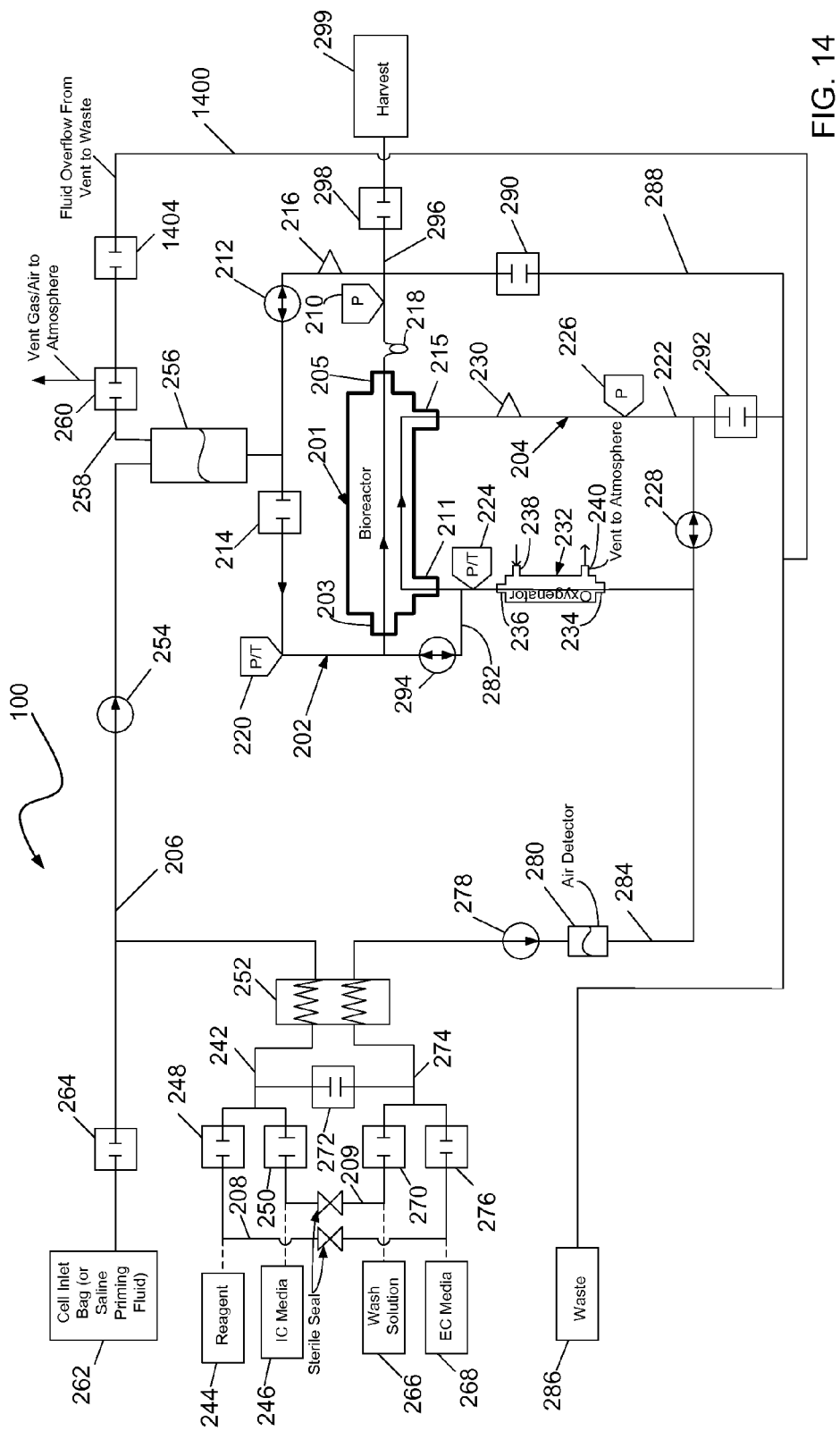
FIG. 14 is another schematic of an embodiment of a cell expansion system.

With reference now to FIG. 14, another schematic of an embodiment of a CES 100 is shown. In the system configuration shown in FIG. 14, a waste line 1400 is provided between the air removal chamber 256 and the waste bag 286 for conveying any fluid that should happen to be expelled from the vent aperture 1224 of the air removal chamber 256. A check valve 1404 may be used to prevent backwards fluid flow from the waste line 1400 to the air valve 260 and/or the air removal chamber 256.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The one or more present inventions, in various embodiments, include components, methods, processes, systems and/or apparatus substantially as depicted and described herein, including various embodiments, subcombinations, and subsets thereof. Those of skill in the art will understand how to make and use the present invention after understanding the present disclosure.

The present invention, in various embodiments, includes providing devices and processes in the absence of items not depicted and/or described herein or in various embodiments hereof, including in the absence of such items as may have been used in previous devices or processes (e.g., for improving performance, achieving ease and/or reducing cost of implementation).

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A cell expansion machine, wherein the cell expansion machine comprises a plurality of fluid level sensors, comprising:
    a tubing-organizer; and
    a fluid conveyance system at least partially attached to the tubing-organizer, the fluid conveyance system comprising:
        a fluid containment member including a containment wall defining a fluid containment chamber therein, wherein a width of the fluid containment chamber increases from a bottom of the fluid containment member to a top of the fluid containment member, wherein a height of the fluid containment chamber is greater than about five times an average width of the fluid containment chamber, and wherein the fluid containment member includes a plurality of apertures through the containment wall including:
            (a) a first aperture and a second aperture, the first aperture and the second aperture located adjacent to one another and situated at a bottom of the fluid containment member, the first aperture adapted to allow a cell-containing fluid to enter the fluid containment member, and the second aperture adapted to allow the cell-containing fluid to exit the fluid containment member, wherein the first aperture and the second aperture are separated from one another by an aperture separator wall, the aperture separator wall comprising a ridge portion extending into the fluid containment chamber, the ridge portion comprising a first slope face and a second slope face, and wherein the first slope face is oriented at an angle of about 90 degrees relative to the second slope face; and
            (b) a venting aperture located above the first aperture and above the second aperture;
        a length of tubing fluidly associated with the fluid containment member; and
        a bioreactor fluidly associated with the length of tubing and with the fluid containment member;
    wherein the tubing-organizer and the fluid conveyance system are adapted to be detachably-attached to the cell expansion machine, and wherein the tubing-organizer comprises a plurality of sensor ports to provide access through a wall of the tubing-organizer to allow the plurality of fluid level sensors on the cell expansion machine to read a level of the cell-containing fluid in the fluid containment member.

2. The cell expansion machine of claim 1, wherein the first aperture and the second aperture are separated by a separation distance $D_s$ of less than about twice the diameter $D_1$ of the first aperture.

3. The cell expansion machine of claim 1, wherein the plurality of fluid level sensors comprises at least two ultrasonic fluid level sensors.

4. The cell expansion machine of claim 3, wherein a first ultrasonic fluid level sensor of the plurality of fluid level sensors is located at a first distance of about ¼ of the height of the fluid containment chamber from the bottom of the fluid containment chamber.

5. The cell expansion machine of claim 4, wherein a second ultrasonic fluid level sensor of the plurality of fluid level sensors is located at a second distance of about ¾ of the height of the fluid containment chamber from the bottom of the fluid containment chamber.

6. The cell expansion machine of claim 3, wherein a top of the ridge portion is situated below a bottom-most ultrasonic fluid level sensor, and wherein the bottom-most ultrasonic fluid level sensor is located at a first distance of about ¼ of the height of the fluid containment chamber from the bottom of the fluid containment chamber.

7. The cell expansion machine of claim 3, further comprising:
    a pump, wherein a pumping rate of the pump modifies the level of the cell-containing fluid within the fluid containment chamber.

8. A method of preventing migration of a gas to a bioreactor within a fluid conveyance system in a cell expansion system, the method comprising:
    detachably-attaching a tubing-organizer of a premounted fluid conveyance assembly to a cell expansion machine of the cell expansion system, wherein the cell expansion machine comprises a plurality of fluid level sensors, and wherein the tubing-organizer comprises a plurality of sensor ports to provide access through a wall of the tubing-organizer to allow the plurality of fluid level sensors on the cell expansion machine to measure a level of a cell-containing fluid in a fluid containment member, wherein the fluid containment member is fluidly associated with the bioreactor and with a fluid conveyance conduit within the fluid conveyance system, and wherein the fluid containment member is connected to the tubing-organizer, the fluid containment member comprising:
        a bubble release chamber, wherein a width of the bubble release chamber increases from a bottom of the fluid containment member to a top of the fluid containment member, wherein a height of the bubble release chamber is greater than about five times an average width of the bubble release chamber; and a first aperture and a second aperture located at a bottom of the fluid containment member and fluidly associated with the bubble release chamber, the first aperture and the second aperture located adjacent to one another, the first aperture adapted to allow the cell-containing fluid to enter the fluid containment member, and the second aperture adapted to allow the cell-containing fluid to exit the fluid containment member, wherein the first aperture and the second aperture are separated from one another by an aperture separator wall having a ridge portion extending into the bubble release chamber, wherein the ridge portion comprises a first slope face and a second slope face, and wherein the first slope face is oriented at an angle of about 90 degrees relative to the second slope face;

after detachably-attaching the tubing organizer to the cell expansion machine of the cell expansion system, pumping the cell-containing fluid from the fluid conveyance conduit through the first aperture and into the bubble release chamber, wherein the cell-containing fluid enters the bubble release chamber moving upward;

venting a gas released from the cell-containing fluid within the bubble release chamber through a vent aperture located above the first aperture and above the second aperture; and causing the cell-containing fluid to flow out of the second aperture.

9. The method of claim 8, further comprising measuring the level of the cell-containing fluid within the bubble release chamber.

10. The method of claim 9, wherein the measuring is performed by operating and monitoring the plurality of fluid level sensors, and wherein the plurality of fluid level sensors comprises at least two ultrasonic fluid level sensors.

11. The method of claim 10, further comprising using data from the at least two ultrasonic fluid level sensors to adjust a pumping rate of at least one pump on the cell expansion machine in order to modify the level of the cell-containing fluid within the bubble release chamber.

12. The method of claim 8, further comprising:

expanding a first set of cells using a first premounted fluid conveyance assembly; and expanding a second set of cells without sanitizing the cell expansion machine after the expanding the first set of cells, wherein the expanding the second set of cells comprises:

interchanging the first premounted fluid conveyance assembly for a second premounted fluid conveyance assembly.

\* \* \* \* \*